(12) United States Patent
Fox et al.

(10) Patent No.: US 8,808,380 B2
(45) Date of Patent: Aug. 19, 2014

(54) METHOD AND APPARATUS FOR AN OSTEOTOMY FIXATION OR ARTHRODESIS CAGE

(75) Inventors: William Casey Fox, Pipe Creek, TX (US); David Joseph Pancratz, Helotes, TX (US)

(73) Assignee: William Casey Fox, Pipe Creek, TX (US)

( * ) Notice: Subject to any disclaimer, the term of this patent is extended or adjusted under 35 U.S.C. 154(b) by 350 days.

(21) Appl. No.: 11/895,671

(22) Filed: Aug. 27, 2007

(65) Prior Publication Data

US 2009/0062916 A1 Mar. 5, 2009

(51) Int. Cl.
*A61F 2/44* (2006.01)

(52) U.S. Cl.
USPC ...................... 623/17.13; 623/17.15

(58) Field of Classification Search
USPC ........................... 623/17.11–17.16
See application file for complete search history.

(56) References Cited

U.S. PATENT DOCUMENTS

| | | | |
|---|---|---|---|
| 4,501,269 A | 2/1985 | Bagby | 606/61 |
| 4,936,848 A | 6/1990 | Bagby | 623/17.16 |
| 5,015,247 A | 5/1991 | Michelson | 606/61 |
| 5,015,255 A | 5/1991 | Kuslich | 128/898 |
| 5,059,193 A | 10/1991 | Kuslich | 606/61 |
| 5,246,443 A * | 9/1993 | Mai | 606/78 |
| 5,263,953 A | 11/1993 | Bagby | 606/61 |
| 5,458,638 A | 10/1995 | Kuslich et al. | 623/17.11 |
| 5,484,437 A | 1/1996 | Michelson | 606/61 |
| 5,489,307 A | 2/1996 | Kuslich et al. | 128/898 |
| 5,489,308 A | 2/1996 | Kuslich et al. | 623/17.11 |
| 5,505,732 A | 4/1996 | Michelson | 606/61 |
| 5,522,899 A | 6/1996 | Michelson | 606/61 |
| 5,554,191 A | 9/1996 | Lahille et al. | 623/17.11 |
| 5,591,235 A | 1/1997 | Kuslich | 606/61 |
| 5,593,409 A | 1/1997 | Michelson | 606/61 |
| 5,609,635 A | 3/1997 | Michelson | 623/17.16 |
| 5,665,122 A | 9/1997 | Kambin | 623/17.16 |
| 5,709,683 A | 1/1998 | Bagby | 606/61 |
| 5,720,748 A | 2/1998 | Kuslich et al. | 606/80 |
| 5,776,199 A | 7/1998 | Michelson | 623/17.61 |
| 5,785,710 A | 7/1998 | Michelson | 606/61 |
| 5,860,973 A | 1/1999 | Michelson | 606/61 |
| 5,885,287 A | 3/1999 | Bagby | 606/61 |
| 5,895,427 A | 4/1999 | Kuslich et al. | 128/898 |
| 5,941,880 A | 8/1999 | Errico et al. | 606/61 |
| 6,010,502 A | 1/2000 | Bagby | 606/61 |
| 6,056,749 A | 5/2000 | Kuslich | 606/61 |
| 6,086,589 A | 7/2000 | Kuslich et al. | 606/61 |

(Continued)

*Primary Examiner* — Eduardo C. Robert
*Assistant Examiner* — Lynnsy Schneider
(74) *Attorney, Agent, or Firm* — Greenberg Traurig, LLP; Ross Spencer Garsson

(57) ABSTRACT

A method and apparatus for an osteotomy fixation or arthrodesis cage allows the adjustment of the relative position of two bone segments while supporting the joining of those bone segments into one structure through the implant and methods described herein. The implant's embodiments fixate to the adjacent bones while inter-positioning its body between the bone segments. This inter-positioning allows anatomical adjustments in the distance between and angle of the bone segments. The adjustment is further enhanced by the use of shape memory materials that when activated through the application of heat energy, transition from a second shape to a first shape while changing the distance between the bones or their relative angle. This method and apparatus can be used on any adjacent bone or bone segments including but not limited to the vertebrae of the spine or long bone such as the tibia or metatarsal.

2 Claims, 41 Drawing Sheets

(56) References Cited

U.S. PATENT DOCUMENTS

| | | | | |
|---|---|---|---|---|
| 6,120,503 | A | 9/2000 | Michelson | 606/61 |
| 6,123,705 | A | 9/2000 | Michelson | 623/17.16 |
| 6,127,597 | A | 10/2000 | Beyar et al. | 606/86 |
| 6,149,650 | A | 11/2000 | Michelson | 623/17.16 |
| 6,149,686 | A | 11/2000 | Kuslich et al. | 623/17.11 |
| 6,159,244 | A | 12/2000 | Suddaby | 623/17.11 |
| 6,174,334 | B1 | 1/2001 | Suddaby | 623/17.11 |
| 6,183,517 | B1 | 2/2001 | Suddaby | 623/17.16 |
| 6,228,085 | B1 | 5/2001 | Theken et al. | 606/61 |
| 6,241,770 | B1 | 6/2001 | Michelson | 623/17.11 |
| 6,264,651 | B1 | 7/2001 | Underwood et al. | 606/32 |
| 6,264,656 | B1 | 7/2001 | Michelson | 606/61 |
| 6,277,112 | B1 | 8/2001 | Underwood et al. | 606/32 |
| 6,283,961 | B1 | 9/2001 | Underwood et al. | 606/41 |
| 6,287,343 | B1 | 9/2001 | Kuslich et al. | 623/17.11 |
| 6,302,914 | B1 | 10/2001 | Michelson | 623/17.16 |
| RE37,479 | E | 12/2001 | Kuslich | 623/17.11 |
| 6,325,805 | B1 | 12/2001 | Ogilvie et al. | 606/25 |
| 6,332,895 | B1 | 12/2001 | Suddaby | 623/17.11 |
| 6,364,880 | B1 | 4/2002 | Michelson | 606/61 |
| 6,371,986 | B1 | 4/2002 | Bagby | 623/17.11 |
| 6,391,058 | B1 | 5/2002 | Kuslich et al. | 623/17.11 |
| 6,395,035 | B2 | 5/2002 | Bresina et al. | 623/17.15 |
| 6,432,107 | B1 | 8/2002 | Ferree | 606/61 |
| 6,436,098 | B1 | 8/2002 | Michelson | 606/61 |
| 6,436,102 | B1 | 8/2002 | Ralph et al. | 606/90 |
| 6,447,544 | B1 | 9/2002 | Michelson | 623/17.16 |
| 6,447,545 | B1 | 9/2002 | Bagby | 623/12.16 |
| 6,447,547 | B1 | 9/2002 | Michelson | 623/17.16 |
| 6,447,548 | B1 | 9/2002 | Ralph et al. | 623/17.16 |
| 6,451,019 | B1 | 9/2002 | Zucherman et al. | 606/61 |
| 6,454,807 | B1 | 9/2002 | Jackson | 623/17.15 |
| 6,468,274 | B1 | 10/2002 | Alleyne et al. | 606/41 |
| 6,471,725 | B1 | 10/2002 | Ralph et al. | 623/17.16 |
| 6,478,801 | B1 | 11/2002 | Ralph et al. | 606/99 |
| 6,478,823 | B1 | 11/2002 | Michelson | 623/17.16 |
| 6,485,517 | B1 | 11/2002 | Michelson | 623/17.11 |
| 6,488,710 | B2 | 12/2002 | Besselink | 623/17.15 |
| 6,491,724 | B1 | 12/2002 | Ferree | 632/17.11 |
| 6,500,173 | B2 | 12/2002 | Underwood et al. | 606/32 |
| 6,500,205 | B1 | 12/2002 | Michelson | 623/17.16 |
| 6,517,544 | B1 | 2/2003 | Michelson | 606/80 |
| 6,537,279 | B1 | 3/2003 | Michelson | 606/79 |
| 6,537,320 | B1 | 3/2003 | Michelson | 623/17.11 |
| 6,540,741 | B1 | 4/2003 | Underwood et al. | 606/32 |
| 6,554,864 | B2 | 4/2003 | Ralph et al. | 623/17.11 |
| 6,558,386 | B1 | 5/2003 | Cragg | 606/61 |
| 6,558,390 | B2 | 5/2003 | Cragg | 606/80 |
| 6,558,423 | B1 | 5/2003 | Michelson | 623/17.11 |
| 6,562,047 | B2 | 5/2003 | Ralph et al. | 606/99 |
| 6,572,619 | B2 | 6/2003 | Santilli | 606/61 |
| 6,607,530 | B1 | 8/2003 | Carl et al. | 606/61 |
| 6,607,559 | B2 | 8/2003 | Ralph et al. | 623/17.16 |
| 6,616,666 | B1 | 9/2003 | Michelson | 606/61 |
| 6,620,155 | B2 | 9/2003 | Underwood et al. | 606/32 |
| 6,623,525 | B2 | 9/2003 | Ralph et al. | 623/17.16 |
| 6,648,915 | B2 | 11/2003 | Sazy | 623/17.11 |
| 6,652,584 | B2 | 11/2003 | Michelson | 623/17.11 |
| 6,656,178 | B1 | 12/2003 | Veldhuizen et al. | 606/616 |
| 6,689,167 | B2 | 2/2004 | Bagby | 623/17.11 |
| 6,695,760 | B1 | 2/2004 | Winkler et al. | 600/7 |
| 6,706,044 | B2 | 3/2004 | Kuslich et al. | 606/61 |
| 6,709,458 | B2 | 3/2004 | Michelson | 623/17.15 |
| 6,712,811 | B2 | 3/2004 | Underwood et al. | 606/31 |
| 6,716,247 | B2 | 4/2004 | Michelson | 623/17.16 |
| 6,726,684 | B1 | 4/2004 | Woloszko | 606/32 |
| 6,730,127 | B2 | 5/2004 | Michelson | 623/17.16 |
| 6,733,535 | B2 | 5/2004 | Michelson | 623/17.16 |
| 6,740,119 | B2 | 5/2004 | Ralph et al. | 623/17.16 |
| 6,743,255 | B2 * | 6/2004 | Ferree | 623/17.11 |
| 6,749,636 | B2 | 6/2004 | Michelson | 623/17.16 |
| 6,758,849 | B1 | 7/2004 | Michelson | 606/61 |
| 6,767,367 | B1 | 7/2004 | Michelson | 623/17.16 |
| 6,773,437 | B2 | 8/2004 | Ogilvie et al. | 606/75 |
| 6,786,930 | B2 | 9/2004 | Biscup | 623/16.11 |
| 6,793,679 | B2 | 9/2004 | Michelson | 623/17.16 |
| 6,800,092 | B1 | 10/2004 | Williams et al. | 623/17.11 |
| 6,805,716 | B2 | 10/2004 | Ralph et al. | 623/17.16 |
| 6,808,537 | B2 | 10/2004 | Michelson | 623/17.15 |
| 6,814,756 | B1 | 11/2004 | Michelson | 623/17.11 |
| 6,821,298 | B1 | 11/2004 | Jackson | 623/17.15 |
| 6,827,740 | B1 | 12/2004 | Michelson | 623/17.11 |
| 6,827,743 | B2 | 12/2004 | Eisermann et al. | 623/23.54 |
| 6,835,206 | B2 | 12/2004 | Jackson | 623/17.11 |
| 6,849,093 | B2 | 2/2005 | Michelson | 623/17.15 |
| 6,863,689 | B2 | 3/2005 | Ralph et al. | 623/17.16 |
| 6,890,355 | B2 | 5/2005 | Michelson | 623/17.11 |
| 6,890,356 | B2 | 5/2005 | Ralph et al. | 623/17.16 |
| 6,896,680 | B2 | 5/2005 | Michelson | 606/90 |
| 6,921,403 | B2 | 7/2005 | Cragg et al. | 606/86 |
| 6,923,810 | B1 | 8/2005 | Michelson | 606/61 |
| 6,923,811 | B1 | 8/2005 | Carl et al. | 606/61 |
| 6,923,830 | B2 | 8/2005 | Michelson | 623/17.16 |
| 6,929,640 | B1 | 8/2005 | Underwood et al. | 606/32 |
| 6,962,606 | B2 | 11/2005 | Michelson | 623/17.16 |
| 6,966,912 | B2 | 11/2005 | Michelson | 606/80 |
| 6,969,390 | B2 | 11/2005 | Michelson | 606/61 |
| 6,972,019 | B2 | 12/2005 | Michelson | 606/61 |
| 6,972,035 | B2 | 12/2005 | Michelson | 623/17.11 |
| 6,976,949 | B2 | 12/2005 | Winkler et al. | 600/7 |
| 6,981,975 | B2 | 1/2006 | Michelson | 606/99 |
| 6,986,772 | B2 | 1/2006 | Michelson | 606/90 |
| 7,008,453 | B1 | 3/2006 | Michelson | 623/17.16 |
| 7,014,633 | B2 | 3/2006 | Cragg | 604/500 |
| 7,018,415 | B1 | 3/2006 | McKay | 623/17.15 |
| 7,033,394 | B2 | 4/2006 | Michelson | 623/17.11 |
| 7,041,135 | B2 | 5/2006 | Michelson | 623/17.11 |
| 7,044,971 | B2 | 5/2006 | Suddaby | 623/17.15 |
| 7,056,342 | B2 | 6/2006 | Michelson | 623/17.11 |
| 7,060,073 | B2 | 6/2006 | Frey et al. | 606/85 |
| 7,066,961 | B2 | 6/2006 | Michelson | 623/17.16 |
| 7,097,648 | B1 | 8/2006 | Gluberman et al. | 606/99 |
| 7,104,986 | B2 | 9/2006 | Houda et al. | 606/32 |
| 2005/0222683 | A1 * | 10/2005 | Berry | 623/17.13 |
| 2007/0179611 | A1 * | 8/2007 | DiPoto et al. | 623/17.11 |
| 2007/0239278 | A1 * | 10/2007 | Heinz | 623/17.15 |
| 2008/0114367 | A1 * | 5/2008 | Meyer | 606/90 |

* cited by examiner

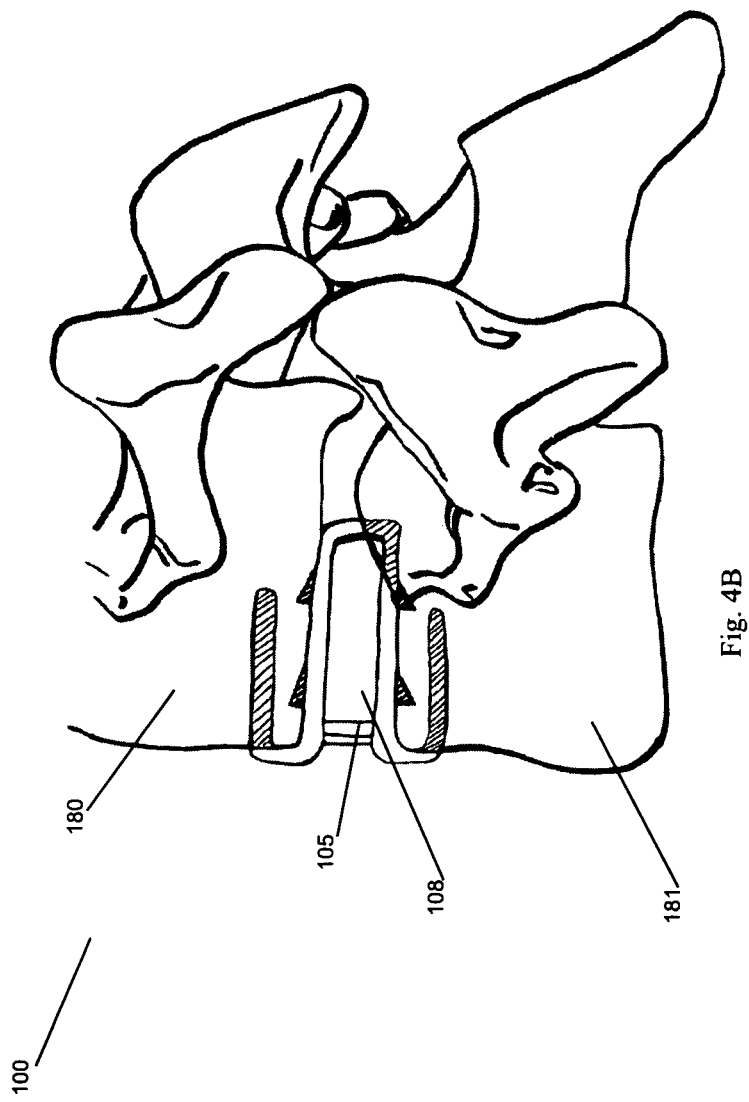

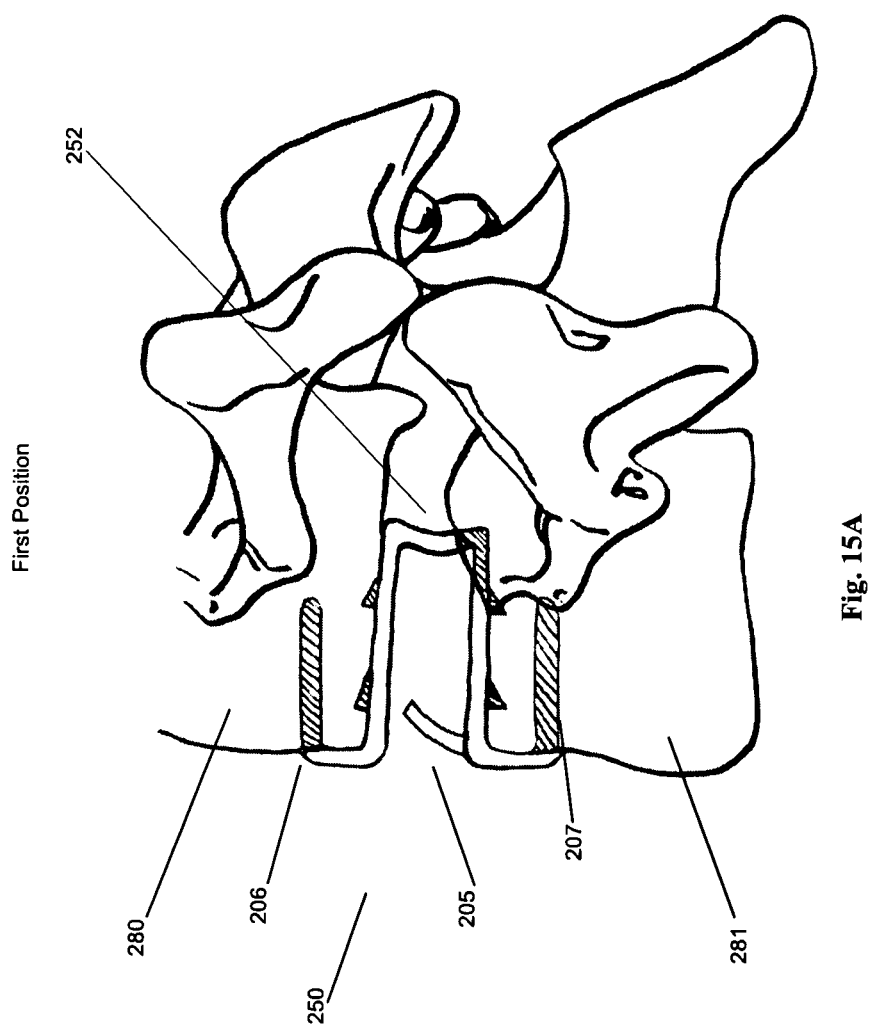

Improperly Curved Spine
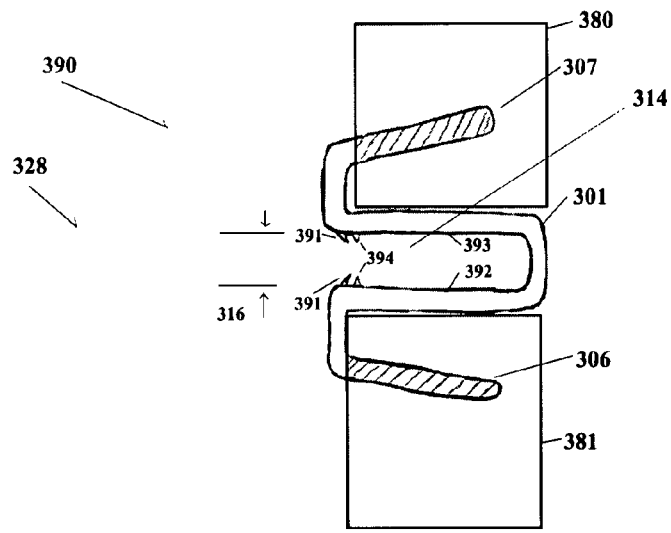
Fig. 19A
Properly Curved Spine
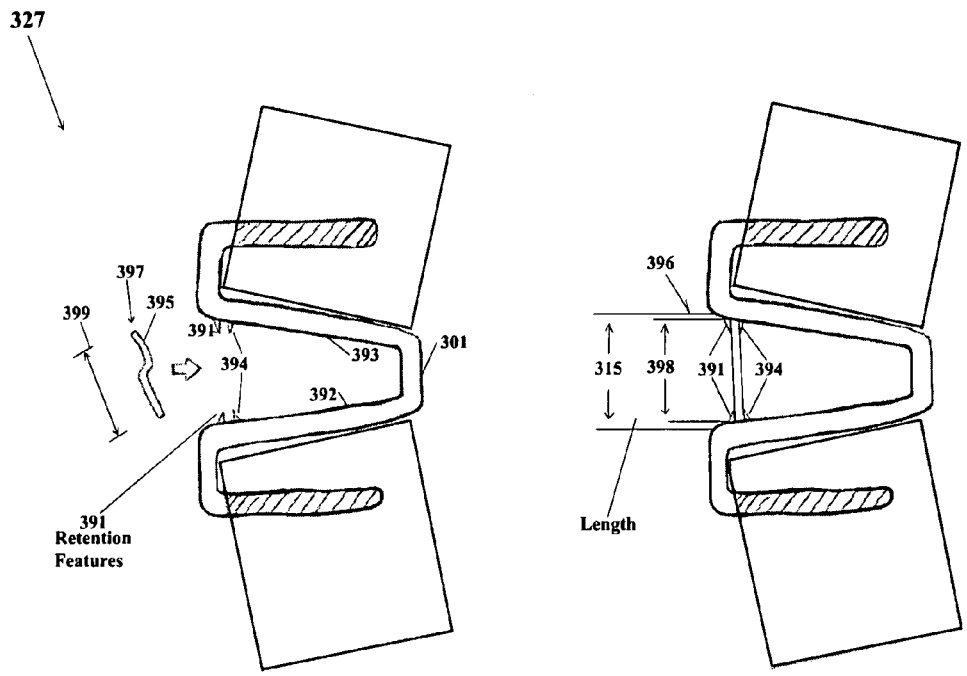
Fig. 19B
Fig. 19C

US 8,808,380 B2

METHOD AND APPARATUS FOR AN OSTEOTOMY FIXATION OR ARTHRODESIS CAGE

BACKGROUND OF THE INVENTION

1. Field of the Invention

The present invention relates to bone fixation devices for the stabilization, orientation and fusion of diseased joints (arthrodesis) or surgical cuts in bone (osteotomies).

2. Description of the Related Art

Repair of bone fractures, osteotomies, or the joining of two bone across a joint are long practiced medical techniques. Often these repairs can be facilitated by immobilization with a splint or cast but often require surgical exposure of the bone and fixation with biocompatible implants designed to reduce (bring together) and hold two or more bony structures.

Wire fixation wires, pins, screws, staples, plates and rods have a long history of use. In spite of these technologies healing sometimes does not occur and the anatomy of the healed bone is often abnormal. The prior art is replete with examples of devices that hold the bones together, but is more limited in references to those devices that present a goal of achieving anatomical adjustments.

In the prior art, U.S. Pat. No. 6,127,597 to Beyar describes systems for the percutaneous bone and spinal stabilization, fixation and repair through using devices that are placed in the medullary cavity of bone and expanded to engage and hold the bone segments. Described are self expanding implants, implants expandable by external power, and solid phase formation devices that expand. Though some of the embodiments utilize shape memory metals such as nitinol as the mechanism for expansion all suffer from a limited ability to provide fixation to the bone segments or anatomical correction.

U.S. Pat. No. 6,773,437 B2 describes a shape memory metal fixation staple and method for correcting deformities of the growing adolescent but does not correct the patient's anatomy through the use of the implant, but restricts the growth of a portion of the spine so that the deformity is corrected over years as the child grows. Once the correction is achieved, the implants are removed. This fixation implant that has an anatomical goal suffers from the delay in the correction and the removal of the implant. The implant alone does not achieve the anatomical correction, the growth of the skeleton does.

Implants that provide fixation and anatomical correction of the spine are described in U.S. Pat. No. 6,264,656 B1, U.S. Pat. No. 6,923,830 B2 and U.S. Pat. No. 7,003,394 B2 by Michelson; U.S. Pat. No. 6,743,255 B2 by Ferree and U.S. Pat. No. 6,656,178 B1 by Veldhuizen, and there are several that expand U.S. Pat. No. 6,488,710 by Besselink, U.S. Pat. No. 6,835,206 B2 by Jackson, and U.S. Pat. No. 7,018,415 B1 by McKay, but are all limited in use by the static nature of their anatomical correction, fixation elements that are separate components or fixation elements that are limited in their fixation ability, such as grooves, slots, ridges or external threads. Though these devices have fixation features and an anatomical form factor they have a history of failure due to the poor fixation ability of external threads, slots and rough surfaces and are limited by their form so as to fit the anatomy versus effect the anatomy.

The subject invention overcomes the history or poor fixation with these types of devices and allows the surgeon to effect the anatomy and relative position of the bone segments by actively changing the implant shape in the spinal disk space or space between bone created with an osteotomy or resection of a joint.

SUMMARY OF THE INVENTION

In accordance with the present invention, bone fixation devices for the stabilization, orientation and fusion of diseased joints (arthrodesis) or surgical cuts in bone (osteotomies) are placed into a bony site to stabilize two adjacent bone segments. These segments could have normal anatomical features such as vertebra of the spine or separated through surgical cuts that subsequently require rejoining.

It is therefore an object of the present invention to join bone segments while allowing the surgeon to control the distance between the segments and the relative orientation of those segments while providing a method of fixation of those segments to one another.

It is a further object of the present invention to allow the surgeon, through the setting of the shape changing temperature of the material used to make the implant and control of the heat applied to the implant, to adjust the orientation, separation and fixation forces applied to the bone segments by the implant.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

BRIEF DESCRIPTION OF THE DRAWINGS

FIG. 4B provides a partial section view of the inter-vertebral cage in the first shape in an installed position according to the first embodiment.

FIG. 15A provides a partial section view of the inter-vertebral cage in a second shape before contraction according to the second embodiment.

FIG. 19A provides a front view of an inter-vertebral cage in a second shape including a separate closeout according to an extension of the third embodiment.

FIG. 19B provides a front view of an inter-vertebral cage in a first shape in an installed position before installation of the separate closeout in a second shape according to the extension of the third embodiment.

FIG. 19C provides a front view of the inter-vertebral cage in a first shape with the installed separate closeout in a first shape according to the extension of the third embodiment.

DETAILED DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. It is further to be understood that the figures are not necessarily to scale, and some features may be exaggerated to show details of particular components or steps.

Figure 1A:
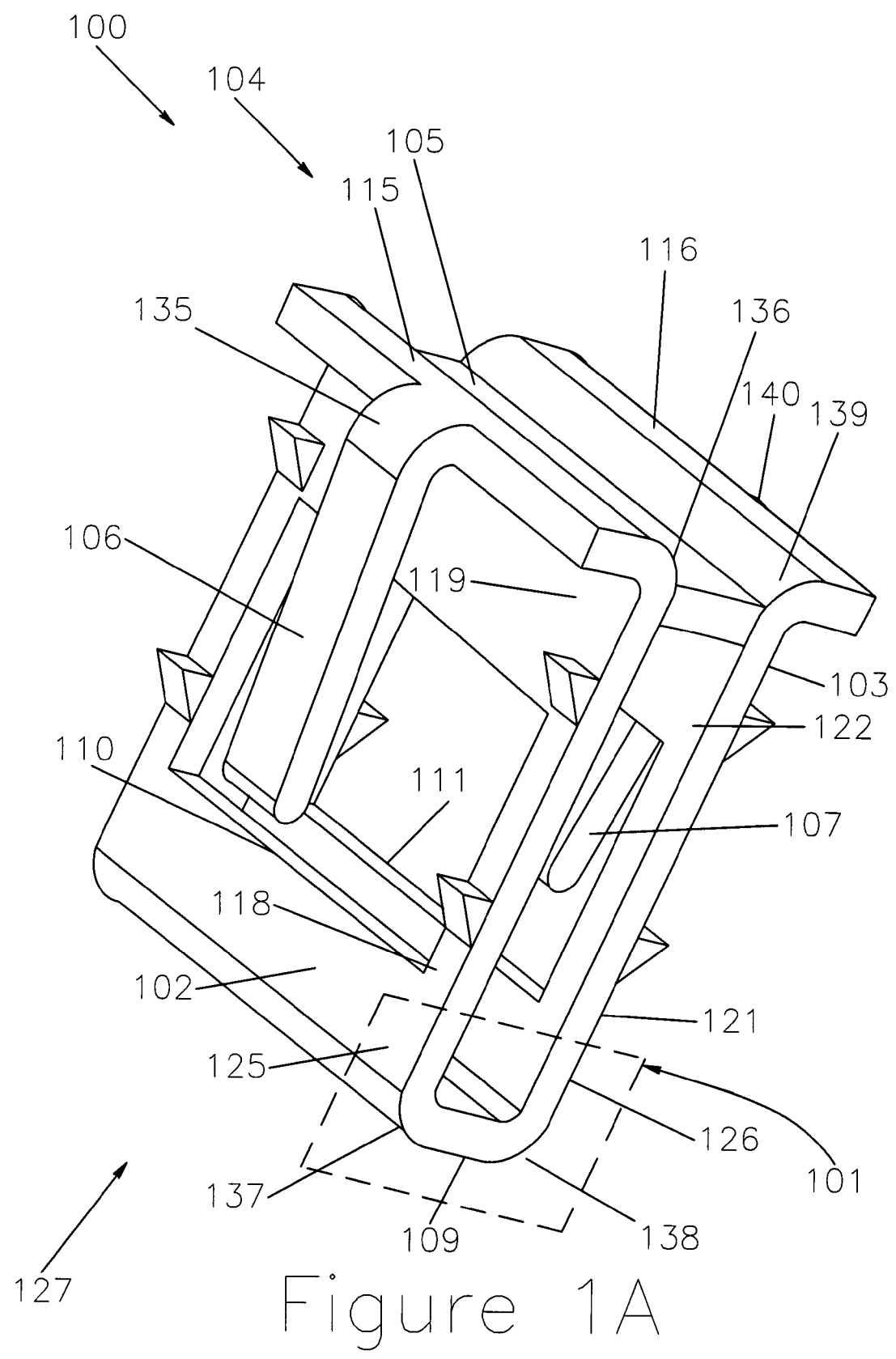
FIG. 1A provides a perspective view of an inter-vertebral cage according to a first embodiment.
Figure 1B:
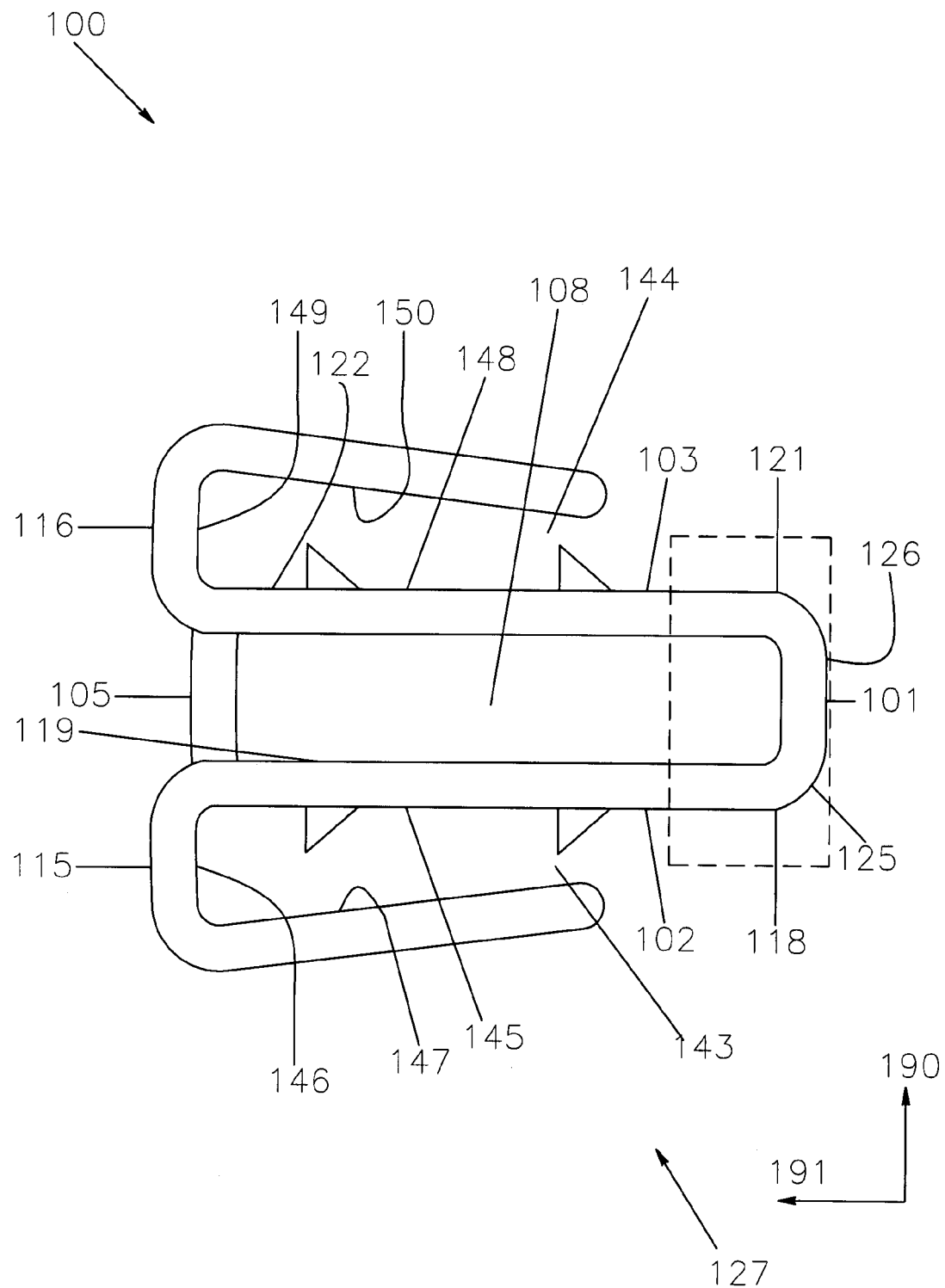
FIG. 1B provides a front view of the inter-vertebral cage in a first shape according to the first embodiment.
Figure 1C:
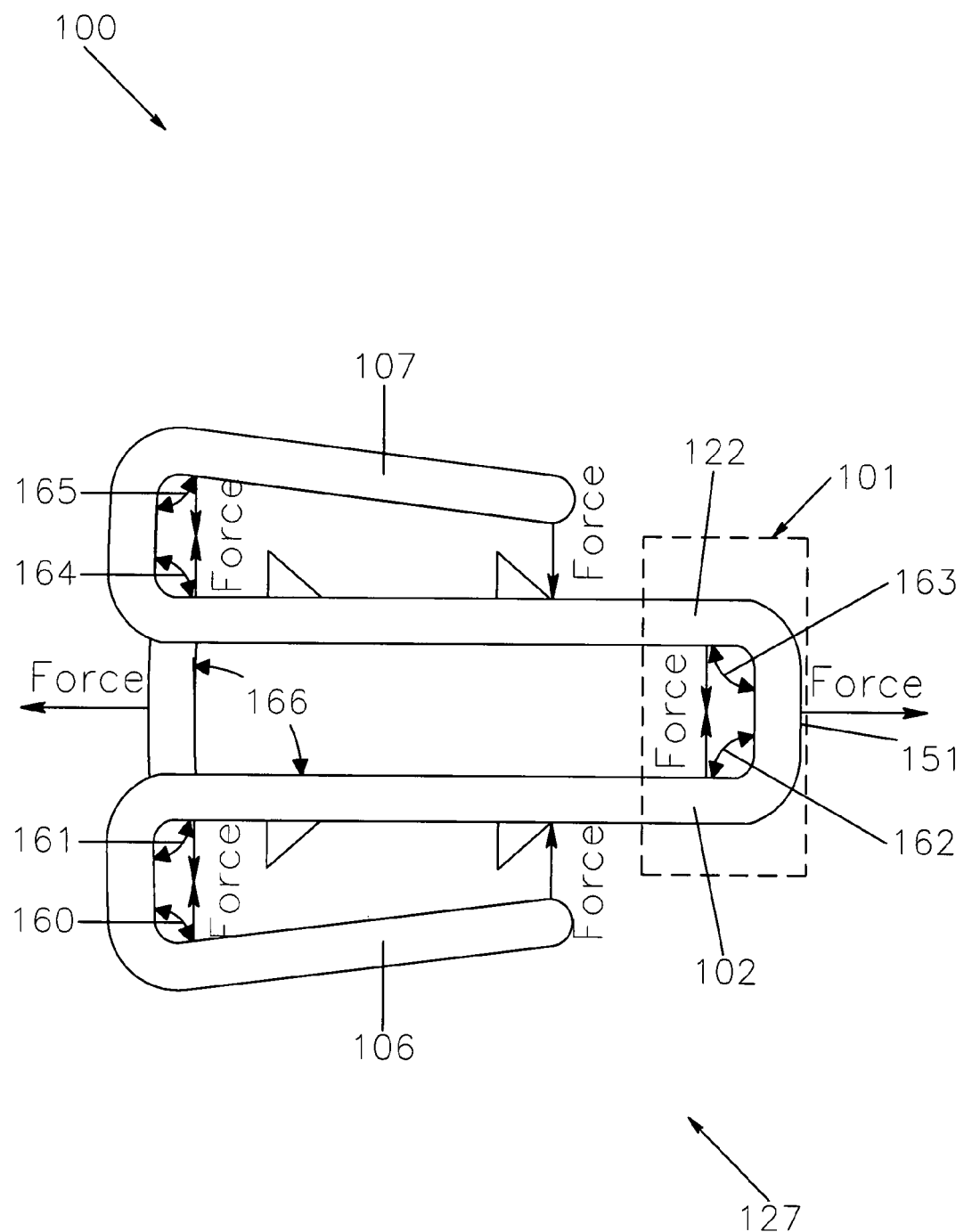
FIG. 1C provides a front view of the inter-vertebral cage in the first shape according to the first embodiment.
Figure 2A:
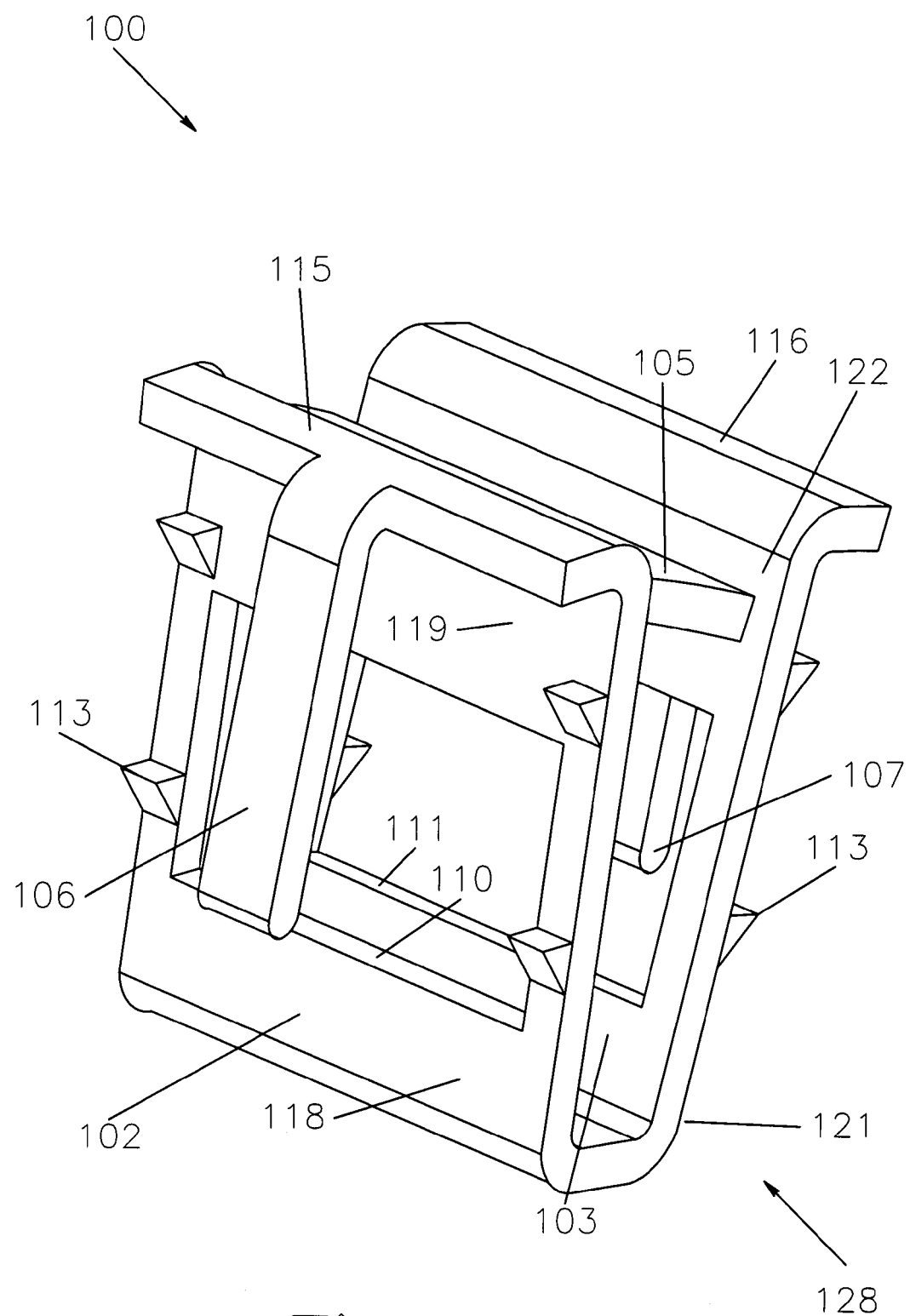
FIG. 2A provides a perspective view of the inter-vertebral cage in a second shape according to the first embodiment.
Figure 2B:
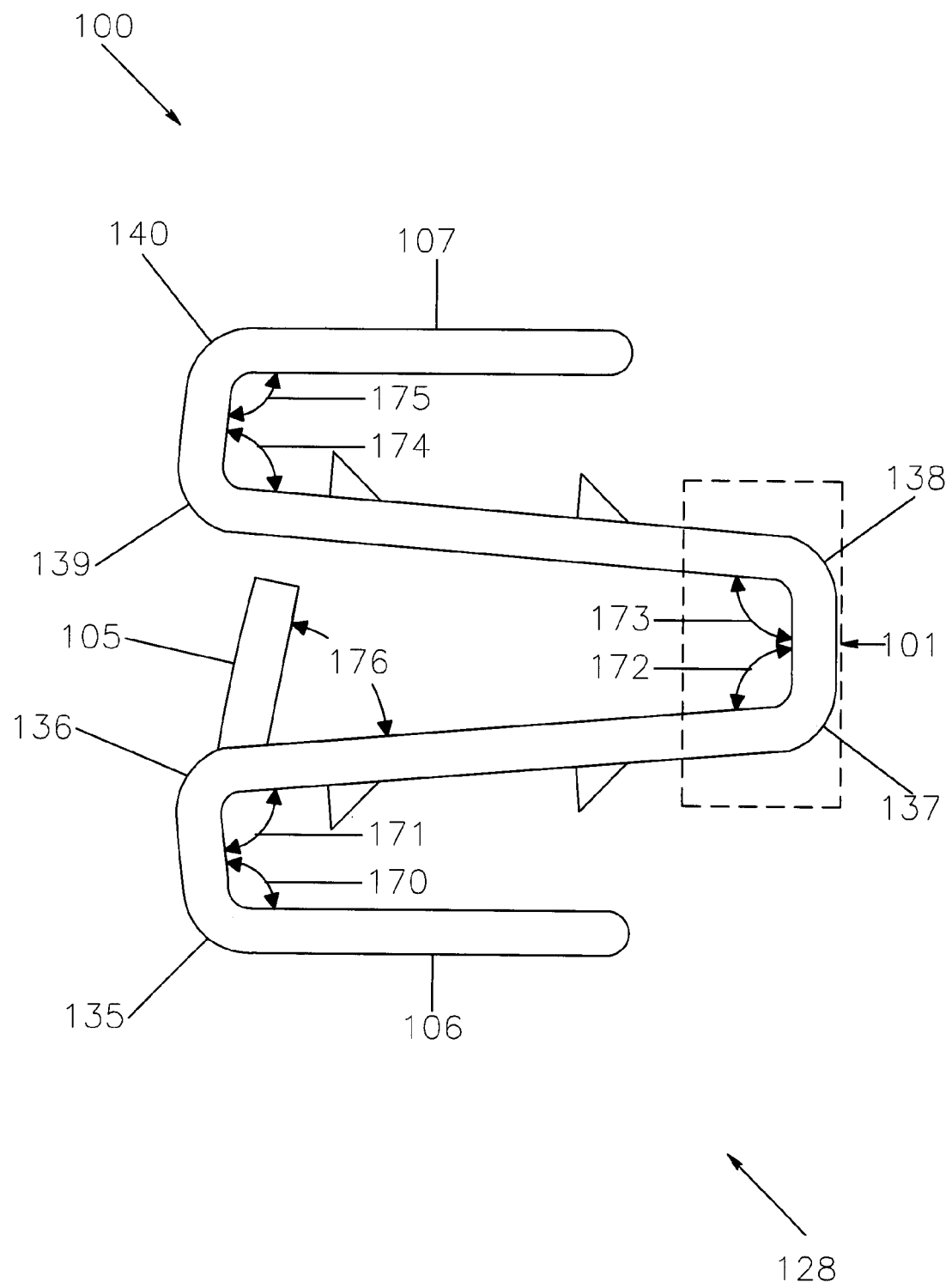
FIG. 2B provides a front view of the inter-vertebral cage in the second shape according to the first embodiment.

As illustrated in FIGS. 1A-2B, an inter-vertebral cage 100 may be constructed from virtually any alloy exhibiting a shape-memory effect. Examples of shape-memory effect materials include, but are not limited to nitinol, AuCd, $FePt_3$, beta Brass, and InTl. Shape memory effect materials allow an object to be: formed in an original shape; deformed while cooled to a martensitic state; then heated to a point where the deformed object phase changes from the martensitic state to an austenitic state, thereby returning the deformed object to its original shape; and when it cools it retains this original shape or first shape. Accordingly, the inter-vertebral cage 100 is formed in an original or first shape 127 (FIGS. 1A-1C), and annealed to set its original shape. The inter-vertebral cage 100, while cold and in its martensitic phase, is then deformed to a second shape 128 (FIGS. 2A-2B). Next, the inter-vertebral cage 100 is heated until it phase changes to an austenitic phase, thereby returning from the deformed or second shape 128 to the original or first shape 127. Finally, the inter-vertebral cage 100 cools whereby the inter-vertebral cage 100 retains the original first shape 127.

While this embodiment has been shown with the inter-vertebral cage 100 moving from the second shape 128 to the first shape 127, it should be apparent that the inter-vertebral cage 100 is usable at virtually any point along the transition between the second shape 128 and the first shape 127. Accordingly, an end-use shape may designate any shape between the second shape 128 and up to and including the first shape 127. The amount of heat energy applied to the deformed shape determines the amount of transition from the second shape 128 to the first shape 127.

The inter-vertebral cage 100 is utilized as a structural component for fixating two vertebrae together in cases where a disc is removed from between the two vertebrae. As shown in FIG. 1A, the inter-vertebral cage 100 includes a body 104 having a first engagement plate 102, a second engagement plate 103, and a spacing member 101 disposed between the first and second engagement plates 102 and 103. The spacing member 101 includes a planar section 109 disposed between a bend 137 and a bend 138. The first engagement plate 102 includes a first end 118 in communication with a first end 125 of the spacing member 101, and a second end 119 in communication with a first stop 115. The second engagement plate 103 includes a first end 121 that is in communication with a second end 126 of the spacing member 101, and a second end 122 that is in communication with a second stop 116. The first and second stops 115 and 116 are substantially planar in shape with curvature as appropriate to match the bone anatomy, and extends as a continuous or interrupted section across the entire length of the second ends 119 and 122 of the first and second engagement plates 102 and 103. The inter-vertebral cage 100 further includes a first leg 106 extending from a central point of the first stop 115, and a second leg 107 extending from a central point of the second stop 116. While this embodiment has been shown with planar stops 115 an 116, one of ordinary skill in the art will recognize that the size and shape of the stops 115 and 116 may be altered to adapt to anatomy or varying attachment conditions, and that virtually any amount of protrusion from the engagement plates may be considered a stop.

For the purpose of clarity and to provide reference points, a horizontal axis 190 and a vertical axis 191 have been provided in FIG. 1B. One of ordinary skill in the art will recognize that references to horizontal and vertical directions are complementary to the cited axes 190 and 191. It should further be understood that a vertical plane is defined as a plane passing through the vertical axis 191 and the horizontal axis 190, and a horizontal plane passes through the horizontal axis 190 and is perpendicular to the vertical plane. Additionally, the term "elevation" is utilized in reference to vertical displacement, wherein a lower elevation is recognized below the horizontal axis 190 and a higher elevation is recognized above the horizontal axis 190. As such, an object may move from a given elevation to a higher or lower elevation.

The inter-vertebral cage 100 further includes a bend 135 disposed between the first leg 106 and the first stop 115, and a bend 136 disposed between the first stop 115 and the first engagement plate 102. The inter-vertebral cage 100 still further includes a bend 139 disposed between the second engagement plate 103 and the second stop 116, and a bend 140 disposed between the second stop 116 and the second leg 107. One of ordinary skill in the art will recognize that the sizes of the bends 135-136 and 139-140, and the ranges of the bends 135-136 and 139-140 may be adjusted to increase or decrease the span of the inter-vertebral cage 100.

The first engagement plate 102 is substantially planar, and includes a first aperture 110. The second engagement plate 103 is substantially planar, and includes a second aperture 111. The first and second apertures 110 and 111 can be round or rectangular in shape, one or multiple, and consuming slightly less than the area of an engagement plate 102 or 103, such that the apertures 110 and 111 are substantially centrally located within the first and second engagement plates 102 and 103. In this example, the first and second engagement plates 102 and 103 are disposed symmetrically about the spacing member 101. While this embodiment has been shown with a spacing member 101 in contact with symmetrical engagement plates 102-103, one of ordinary skill in the art will recognize that the shape, length, and width of the spacing member 101 and the engagement plates 102-103 may be changed to provide increased height, load capability, an increased aperture size, different location on the engagement plates 102-103, or a different geometry. Illustratively, the spacing member 101 may be located differently with respect to the engagement plates 102-103, and does not have to span the entire length of the plates 102-103. Further, the spacing member 101 may be broken up into multiple spacing members 101.

The inter-vertebral cage 100 further includes engagement areas 143 and 144, as shown in FIG. 1B. Engagement area 143 includes a first engagement surface 145, a second engagement surface 146, and a third engagement surface 147. The first engagement surface 145 is disposed on an outer surface of the first engagement plate 102, the second engagement surface 146 is disposed on a side of the first stop 115 nearest the spacing member 101, and the third engagement surface 147 is disposed on a face of the first leg 106 that is nearest the first engagement surface 145, such that an object between the first engagement surface 145 and the third engagement surface 147 is compressed when moving from the second shape to the first shape, and contacts the second engagement surface 146. Similarly, the second engagement area 144 includes a first engagement surface 148, a second engagement surface 149, and a third engagement surface 150. The first engagement surface 148 is disposed on an outer surface of the second engagement plate 103, the second engagement surface 149 is disposed on a face of the second stop 116 that lies nearest the spacing member 101, and the third engagement surface 150 is disposed on an inner face of the second leg 107, such that the third engagement surface 150 is disposed opposite from the first engagement surface 148, and material between the first and third engagement surfaces 148 and 150 is compressed while in contact or close proximity with the second engagement surface 149. While the first and second engagement areas 143-144 have been shown with three engagement surfaces, one of ordinary skill in the art will recognize that the number and locations of the engagement surfaces may vary, depending on the specific configuration, number of legs, and in vivo conditions.

The inter-vertebral cage 100 further includes a closeout 105 that extends from an inner surface of the first engagement plate 102. In this embodiment, the closeout 105 spans the entire length of the first engagement plate 102, and extends toward the second engagement plate 103, such that a cavity 108 is created between the spacing member 101, the first engagement plate 102, the second engagement plate 103, and the closeout 105. While the closeout 105 has been shown as protruding from the first engagement plate 102, one of ordinary skill in the art will recognize that the closeout may extend from other surfaces, and that the closeout 105 may be broken into multiple segments.

The inter-vertebral cage 100 may further include at least one barb 113 disposed on the first engagement surface 145 and the first engagement surface 148. The barbs 113 are oriented such that they restrict the movement of the inter-vertebral cage 100 out of an installed position. One of ordinary skill in the art will recognize that additional barbs 113 may be added to the engagement surface or leg, and utilized to provide increased resistance, and that the sizes of the barbs 113 may be adjusted as necessary to ensure adequate resistance.

In the first shape 127, as shown in FIGS. 1A-1C, the first engagement plate 102 and the spacing member 101 are disposed at an angle 162, and the second engagement plate 103 is disposed at an angle 163 relative to the spacing member 101. In this example, the first engagement plate 102 and the second engagement plate 103 are disposed substantially perpendicular to the spacing member 101 and in proximity to each other, such that the first engagement plate 102 and the second engagement plate 103 are substantially symmetrical about the spacing member 101, and a cavity 108 is created between the first engagement plate 102 and the second engagement plate 103. While the first and second engagement plates 102 and 103 have been shown as being substantially perpendicular to the spacing member 101, one of ordinary skill in the art will recognize that the angles 162 and 163 may be adjusted to adapt to location specific features, or varying angles of correction.

The first stop 115 is disposed at an angle 161 relative to the first engagement plate 102. In this example of the first shape 127, the first stop 115 is disposed substantially perpendicular relative to the first engagement plate 102, and extends away from the second engagement plate 103. Similarly, the second stop 116 is disposed at an angle 164 relative to the second engagement plate 103. In this first shape 127, the second stop 116 is disposed substantially perpendicular to the second engagement plate 103, and extends away from the first engagement plate 102. The first leg 106 is disposed at an angle 160 relative to the first stop 115, and extends downward towards the spacing member 101. In this first shape 127, the angle 160 is approximately sixty degrees. However, one of ordinary skill in the art will recognize that the specific angles of this embodiment may be adjusted to overcome irregular implant site conditions. Similarly, the second leg 107 is disposed at an angle 165 relative to the second stop 116, and also extends towards the spacing member 101. In this first shape 127, the angle 165 is substantially identical to the angle 160, such that the legs 106 and 107 are symmetrical, and apply an evenly distributed load. Additionally, the closeout 105 is substantially planar and is disposed at an angle 166 relative to the first engagement plate 102. In this first shape 127, the angle 166 is substantially ninety degrees, such that the closeout 105 contacts the second engagement plate 103, thereby transferring loads from the first engagement plate 102 to the second engagement plate 103, and from the second engagement plate 103 to the first engagement plate 102. While this embodiment has been shown with a substantially planar closeout 105 disposed at an angle of approximately ninety degrees, one of ordinary skill in the art will recognize that the closeout 105 may be of virtually any shape that provides a closing out function. It should further be understood that the closeout may be disposed at virtually any angle that maintains a stand off from the attaching engagement plate.

In the second shape 128, the inter-vertebral cage 100 is deformed as shown in FIGS. 2A-2B, such that the bends 137 and 138 of the first shape 127 are extended to obtuse angles 172 and 173. Accordingly, in the second shape 128, the first engagement plate 102 is disposed at an angle of one hundred and ten degrees relative to the spacing member 101, and the second engagement plate 103 is likewise disposed at an angle of one hundred and ten degrees relative to the spacing member 101. The bends 136 and 139 are similarly contracted from their positions in the first shape 127 to angles 171 and 174, thereby slightly rotating the first and second stops 115 and 116 towards the spacing member 101. Similarly, the bends 135 and 140 are extended to angles 170 and 175, such that the first and second legs 106 and 107 are disposed at an angle of approximately one hundred and ten degrees relative to their respective stops 115 or 116. Additionally, the closeout 105 is deformed towards the spacing member 101, thereby contracting angle 166 to an angle 176. In this second shape 128, the closeout 105 is disposed at an angle of approximately seventy-five degrees relative to the first engagement plate 102. In this position, the first leg 106 and the second leg 107 are disposed substantially parallel to each other, such that the legs 106 and 107 may be inserted into bones simultaneously. While the engagement plates 102-103 and legs 106-107 have been shown at particular angles relative to the spacing member 101, one of ordinary skill in the art will recognize that other angles are possible, and should be viewed as part of this invention. It should further be recognized that the use of the parallel legs 106 and 107 is conducive to the impaction of the legs 106 and 107 into vertebra or the insertion of the legs 106 and 107 into pre-drilled holes; however, other angles may be utilized to address alternative situations, including the insertion of one leg at a time.

Upon the application of energy, the inter-vertebral cage 100 in the deformed or second shape 128 (deformed martensitic phase), commences to change from the martensitic state to the austenitic state. Upon completion of the austenitic phase change, the inter-vertebral cage 100 has returned to the original or first shape 127. Upon cooling, the inter-vertebral cage 100 retains the original or first shape 127. One of ordinary skill in the art will recognize that upon the transformation of a shape memory alloy to the original shape 127, a force is created, and accordingly, the inter-vertebral cage 100 may be utilized in applications where retaining and residual forces are required.

In this first embodiment, the phase change from the deformed or second shape 128 to the original or first shape 127 creates forces as shown in FIG. 1C. The bend 135 moves from the angle 170 (obtuse angle associated with second shape 128) to a more acute angle 160 (acute angle associated with the first shape 127), thereby rotating the first leg 106 toward the first engagement plate 102. In a similar fashion, the bend 140 moves from the angle 175 (obtuse angle associated with second shape 128) to a more acute angle 165 (acute angle associated with the first shape 127), thereby rotating the second leg 107 towards the second engagement plate 103. The bend 136 moves from the angle 171 (obtuse angle associated with second shape 128) to a smaller angle 161 (associated with the first shape 127). Similarly, the bend 139 moves from the angle 174 (obtuse angle associated with second shape 128) to a smaller angle 164 (associated with the first shape 127). Additionally, the bend 137 moves from angle 172 (obtuse angle associated with second shape 128) to angle 162 (smaller angle associated with first shape 127). Similarly, the bend 138 moves from the angle 173 (obtuse angle associated with second shape 128) to angle 163 (smaller angle associated with first shape 127). Further, the closeout 105 moves from angle 176 (acute angle associated with second shape 128) to the angle 166 (larger angle associated with first shape 127).

In this first embodiment, compressive forces are created between the first engagement surface 145 and the third engagement surface 147. Additionally, compressive forces may be created between the second engagement surface 146 and the third engagement surface 147 as the first leg 106 closes down on material disposed between the first leg 106 and the first engagement plate 102. Compressive forces are also created between the third engagement surface 150 and the first engagement surface 148, and between the third engagement surface 150 and the second engagement surface 149 as the second leg 107 moves towards the second engagement plate 103. Compressive forces are further created between the first engagement plate 102 and the second engagement plate 103 as the bends 137-138 contract to angles 162 and 163, respectively. When the first and second legs 106 and 107 are secured, a thrust force component is created as the inter-vertebral cage 100 moves from the first shape 127 to the second shape 128. The thrust force, shown in FIG. 1C, lies perpendicular to the plane of the spacing member 101 and away from a third engagement area 151. The thrust force is created when the legs 106 and 107 are pinned, and the first and second engagement plates 102 and 103 move towards each other during the shape change.

Figure 3:
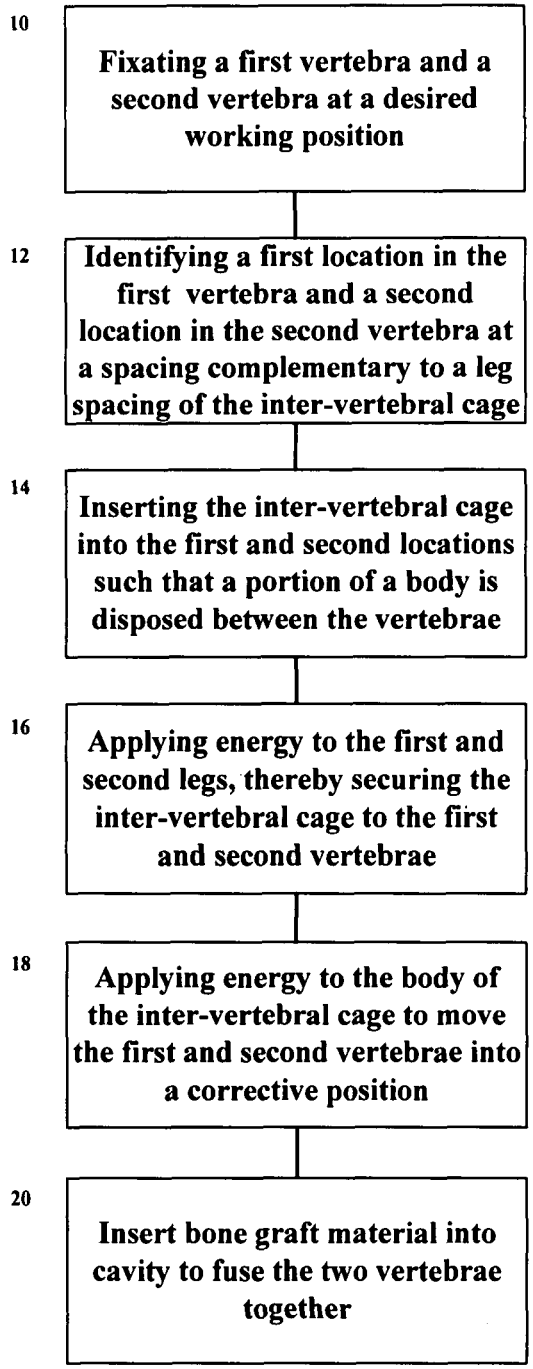
FIG. 3 provides a flowchart illustrating the method steps for utilizing the inter-vertebral cage according to the first embodiment.

FIG. 3 provides a flowchart illustrating the method steps associated with utilizing the inter-vertebral cage 100 to fuse two vertebrae together. The process commences with step 10, wherein a surgeon fixates a first vertebra 180 and a second vertebra 181 at a desired working position. The surgeon continues with step 12, wherein a first location is identified in the first vertebra 180, and a second location is identified in the second vertebra 181 at a spacing complementary to a spacing between the legs 106 and 107 of the inter-vertebral cage 100. The process continues with step 14, wherein the surgeon inserts the legs 106-107 into the first and second locations, such that the first and second engagement plates 102 and 103 are disposed between the first and second vertebrae 180 and 181. In step 16, the surgeon applies energy to the first and second legs 106 and 107 of the inter-vertebral cage 100, thereby securing the inter-vertebral cage 100 to the first and second vertebrae 180 and 181. The process continues with step 18, wherein the surgeon applies energy to the body 104 of the inter-vertebral cage 100 to move the first and second vertebrae 180 and 181 into a desired corrective position. Once the first and second vertebrae 180 and 181 are in the desired corrective position, the surgeon inserts bone graft material into the cavity 108, such that the bone graft material unites with the first and second vertebrae 180 and 181 through the first and second apertures 110 and 111. Upon bone fusion, the graft material and the first and second vertebrae 180 and 181 become a single unit.

Figure 4A:
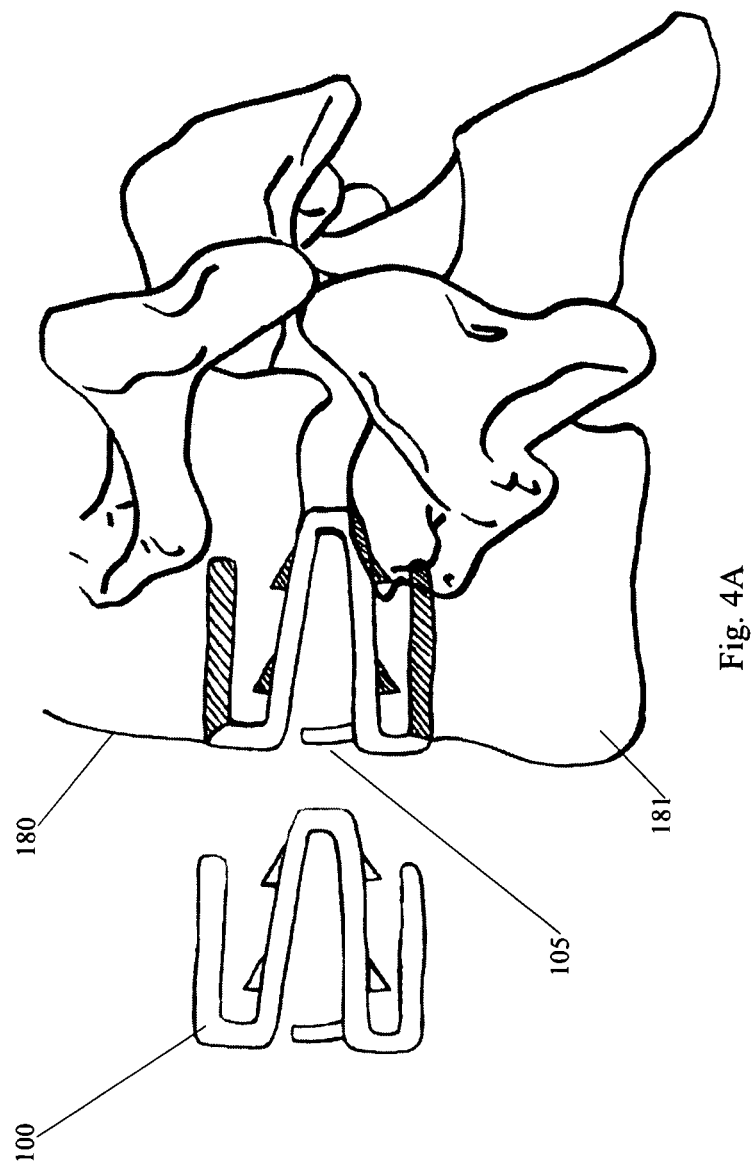
FIG. 4A provides a partial section view of the inter-vertebral cage in the second shape according to the first embodiment.

FIG. 4A provides a side view of the inter-vertebral cage 100 in the second shape 128, wherein the first leg 106 and the second leg 107 are substantially parallel to each other, and the closeout 105 is angled slightly downward. Upon insertion of the first leg 106 into the first location on the first vertebra 180, and the insertion of the second leg 107 into the second location on the second vertebra 181, the body 104 moves between the vertebrae 180 and 181, until the second engagement surface 146 and the second engagement surface 149 contact the respective vertebra 180 or 181. The barbs 113 engage the vertebrae 180 and 181, thereby securing the inter-vertebral cage 100 to the vertebrae 180 and 181. Upon full insertion, the spacing member 101 and the engagement plates 102 and 103 are disposed between the vertebrae 180 and 181. In this position, the closeout 105 does not contact the second engagement plate 103. Upon the application of energy to the legs 106 and 107, the legs 106 and 107 move from the second shape 128 to the first shape 127, thereby drawing the legs 106 and 107 toward the inter-vertebral cage 100, and further securing the inter-vertebral cage 100 to the vertebrae 180 and 181, as shown in FIG. 4B. Upon the application of energy to the body 104, the closeout 105 moves from the second shape 128 to the first shape 127, thereby extending towards the second engagement plate 103, and the bends 137 and 138 contract to the first shape 127, thereby drawing the second engagement plate 103 towards the first engagement plate 102, until the second engagement plate 103 contacts the newly extended closeout 105. At this point, the cavity 108 is substantially closed out, as shown in FIG. 4B. While this embodiment has been shown with bone graft material being inserted after the application of energy to the body 104 of the inter-vertebral cage 100, one of ordinary skill in the art will recognize that bone graft material may be inserted into the cavity 108 at alternate times, or not at all.

Figure 5:
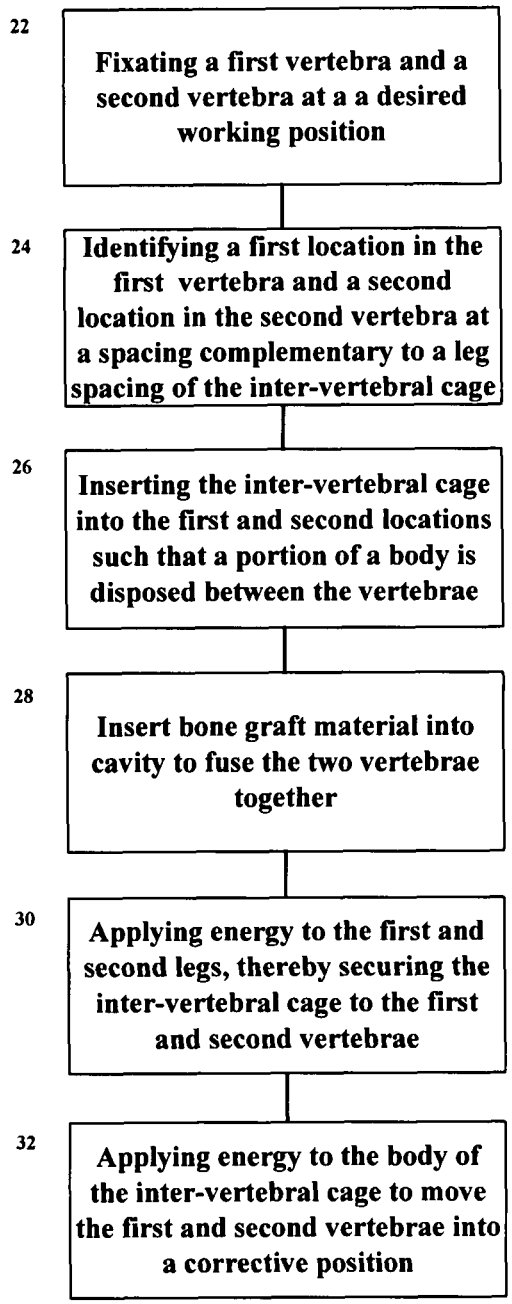
FIG. 5 provides a flowchart illustrating the method steps for utilizing the inter-vertebral cage according to an extension of the first embodiment.

FIG. 5 provides a flowchart illustrating the method steps of the process disclosed in FIG. 3 in an alternate order. In this extension of this first embodiment, bone graft material may be inserted into the cavity 108 before the application of energy to the body 104. The process commences with step 22, wherein a surgeon fixates a first vertebra 180 and a second vertebra 181 at a desired working position. The surgeon continues with step 24, wherein a first location is identified in the first vertebra 180, and a second location is identified in the second vertebra 181 at a spacing complementary to a spacing between the legs 106 and 107 of the inter-vertebral cage 100. The process continues with step 26, wherein the surgeon inserts the inter-vertebral cage 100 into the first and second locations, such that the body 104 is disposed between the first and second vertebrae 180 and 181. The surgeon then inserts bone graft material into the cavity 108 to promote fusion of the vertebrae 181 and 180, step 28. In step 30, the surgeon applies energy to the first and second legs 106 and 107 of the inter-vertebral cage 100, thereby securing the inter-vertebral cage 100 to the first and second vertebrae 180 and 181. The process continues with step 32, wherein the surgeon applies energy to the body 104 of the inter-vertebral cage 100 to move the first and second vertebrae 180 and 181 into a desired corrective position. While this extension of the first embodiment has been shown with the insertion of bone graft material before the application of energy to the inter-vertebral cage 100, one of ordinary skill in the art will recognize that a surgeon will add bone graft material after moving the first and second vertebrae 180 and 181 into the desired corrective position if an improper amount of bone graft material remains in the cavity 108. Accordingly, this extension of the first embodiment may include an additional step of adding additional bone graft material after step 32. The bone graft material unites with the first and second vertebrae 180 and 181 through the first and second apertures 110 and 111. Upon bone fusion, the graft material and the first and second vertebrae 180 and 181 become a single unit. One of ordinary skill in the art will further recognize that either process may be employed to achieve similar results. While the method of implanting inter-vertebral cage 100 has been presented, one of ordinary skill in the art will further recognize that the sequence of steps may be changed to meet a specific clinical need.

Figure 6A:
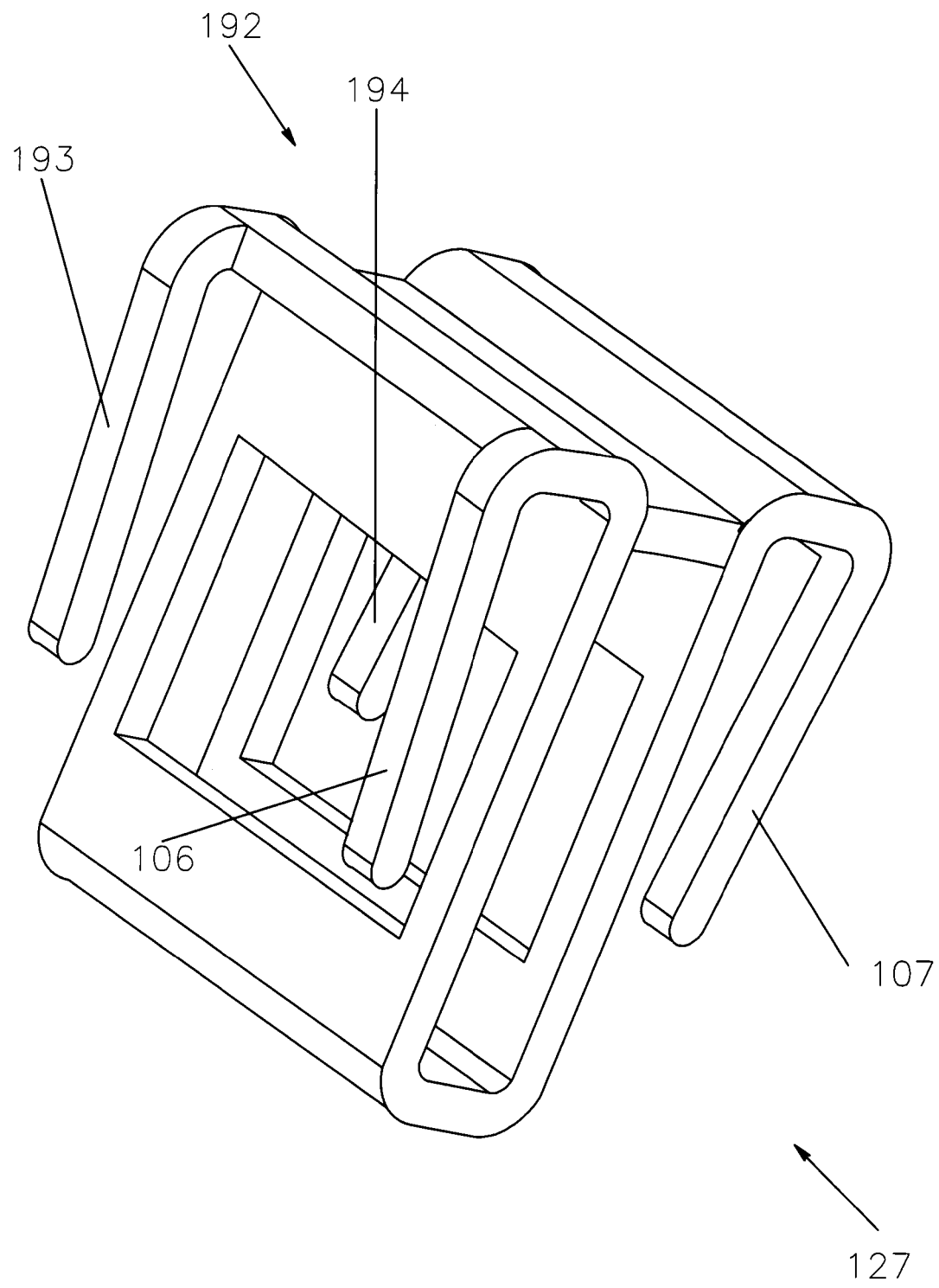
FIG. 6A provides a perspective view of an inter-vertebral cage according to an extension of the first embodiment.
Figure 6B:
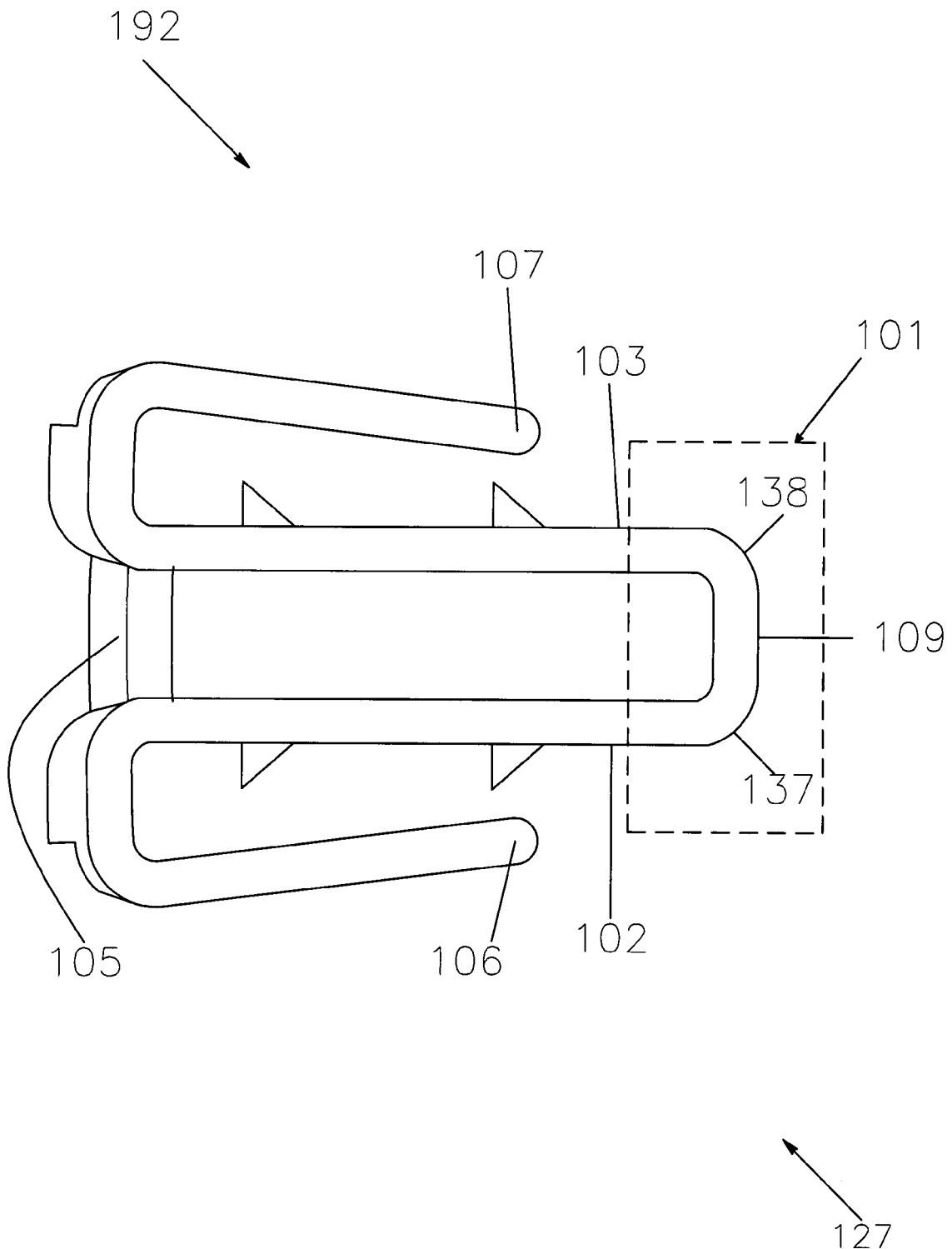
FIG. 6B provides a front view of the inter-vertebral cage in a first shape according to the extension of the first embodiment.
Figure 6C:
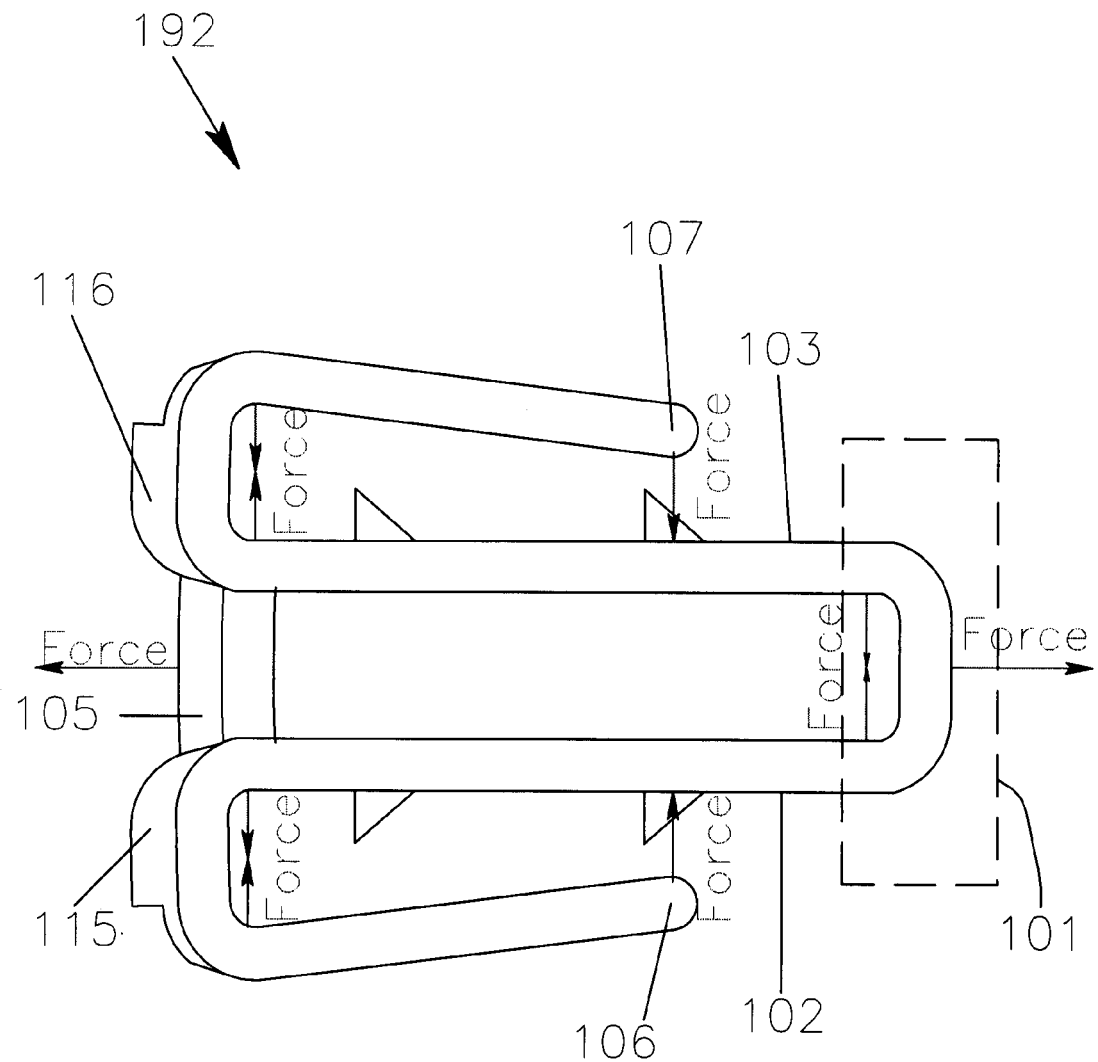
FIG. 6C provides a front view of the inter-vertebral cage in the first shape according to an extension of the first embodiment.

In an extension of the first embodiment, an inter-vertebral cage 192 is substantially identical to the inter-vertebral cage 100, however the inter-vertebral cage 192 includes additional legs. Accordingly, like parts have been referenced with like numerals. As shown in FIGS. 6A-6C, the inter-vertebral cage 192 includes a spacing member 101 attached to first and second engagement plates 102 and 103, and first and second stops 115 and 116 disposed at the ends of the first and second engagement plates 102 and 103. The inter-vertebral cage 192 further includes a first leg 106, a second leg 107, a third leg 193, and a fourth leg 194. The first leg 106 and the third leg 193 extend from the first stop 115 in a similar fashion to the inter-vertebral cage 100, however, the first and third legs 106 and 193 are disposed at extreme ends of the first stop 115. Similarly, the second and fourth legs 107 and 194 are disposed at extreme ends of the second stop 116. One of ordinary skill in the art will recognize that other embodiments that include fewer or a greater number of legs are within the scope of this invention. Additionally, it should further be understood that while these legs are shown as being symmetrical, and balanced, it is possible to provide an odd number of legs, as dictated by body conditions.

Figure 7A:
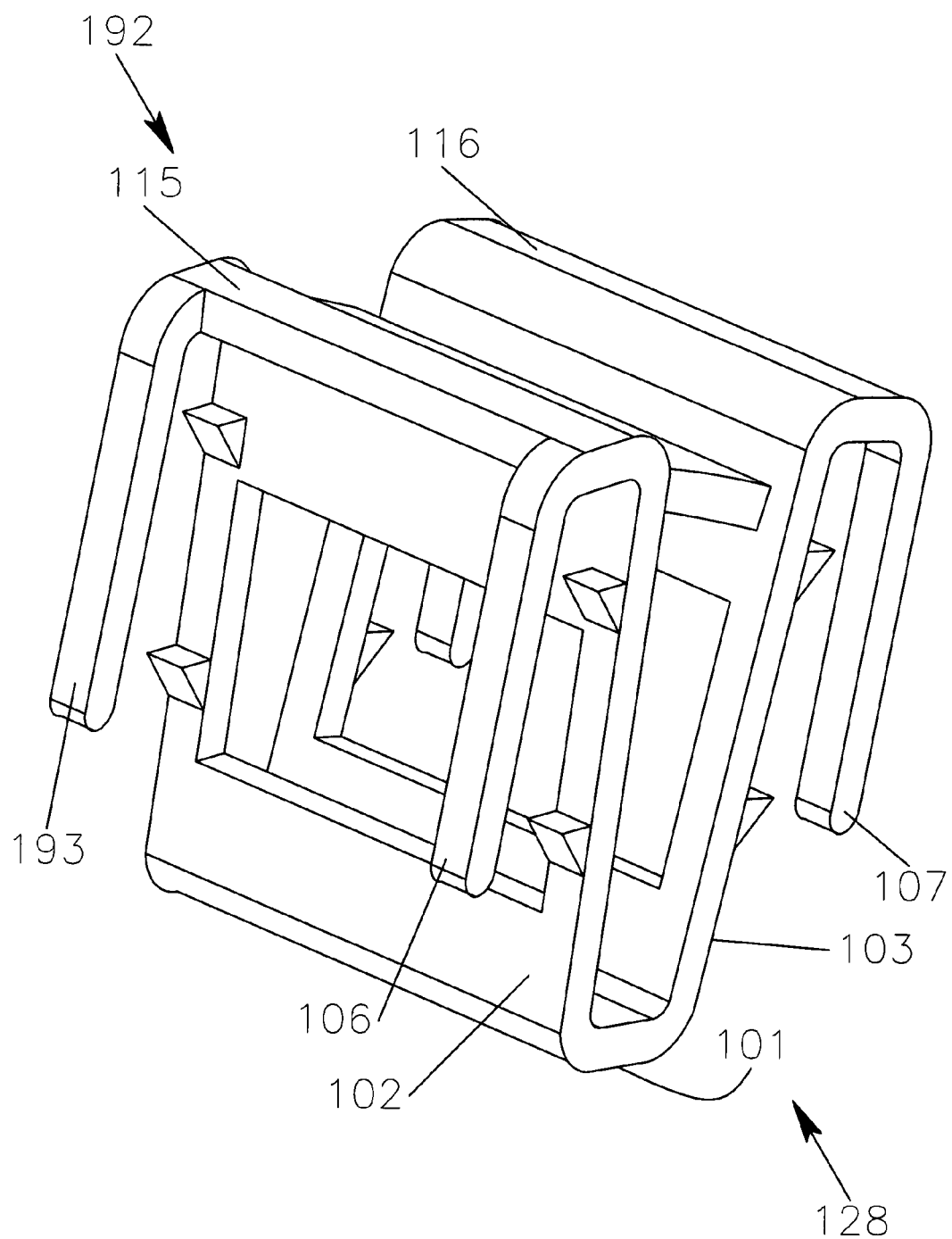
FIG. 7A provides a perspective view of the inter-vertebral cage in a second shape according to an extension of the first embodiment.
Figure 7B:
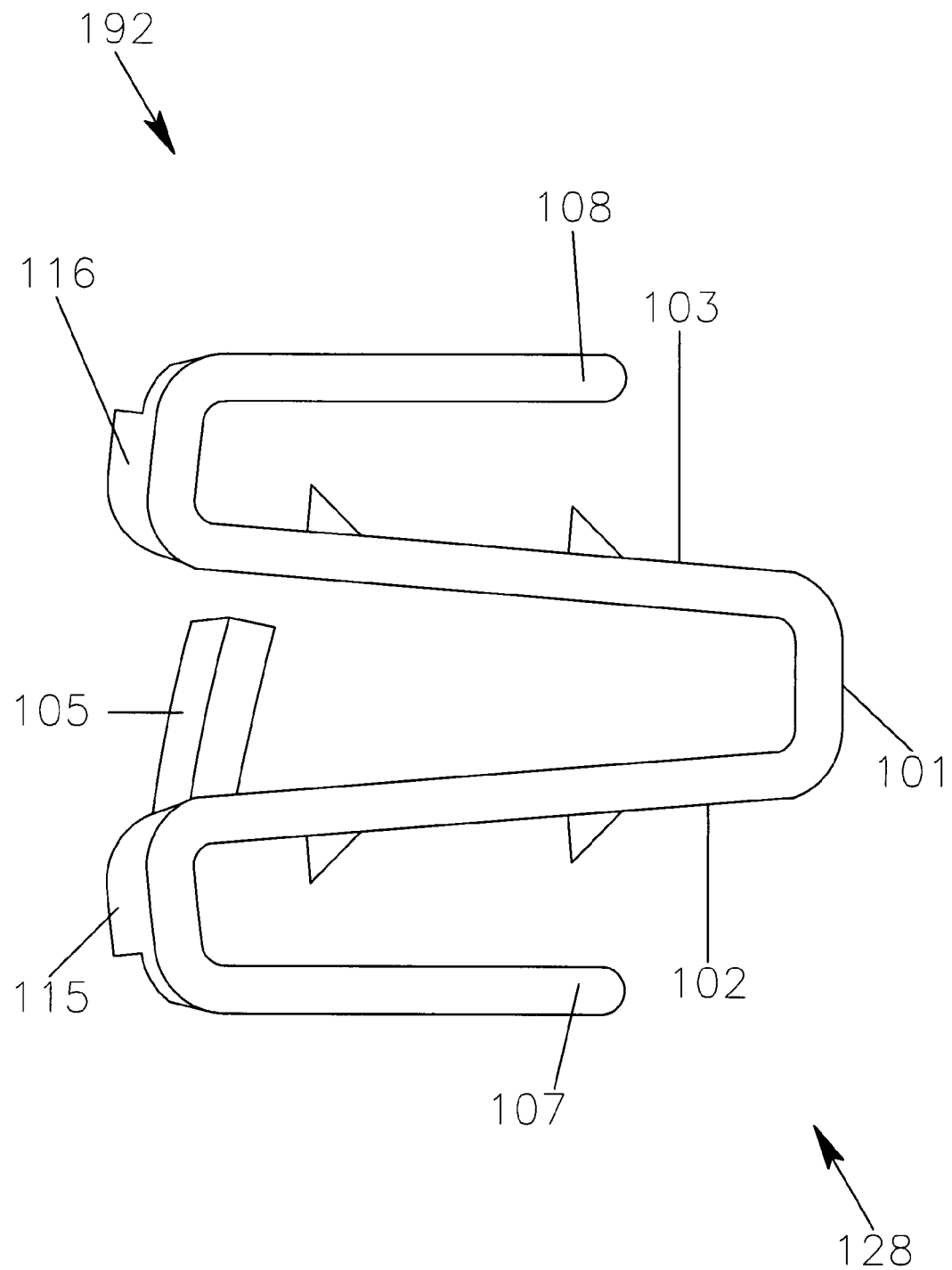
FIG. 7B provides a front view of the inter-vertebral cage in the second shape according to an extension of the first embodiment.
Figure 8A:
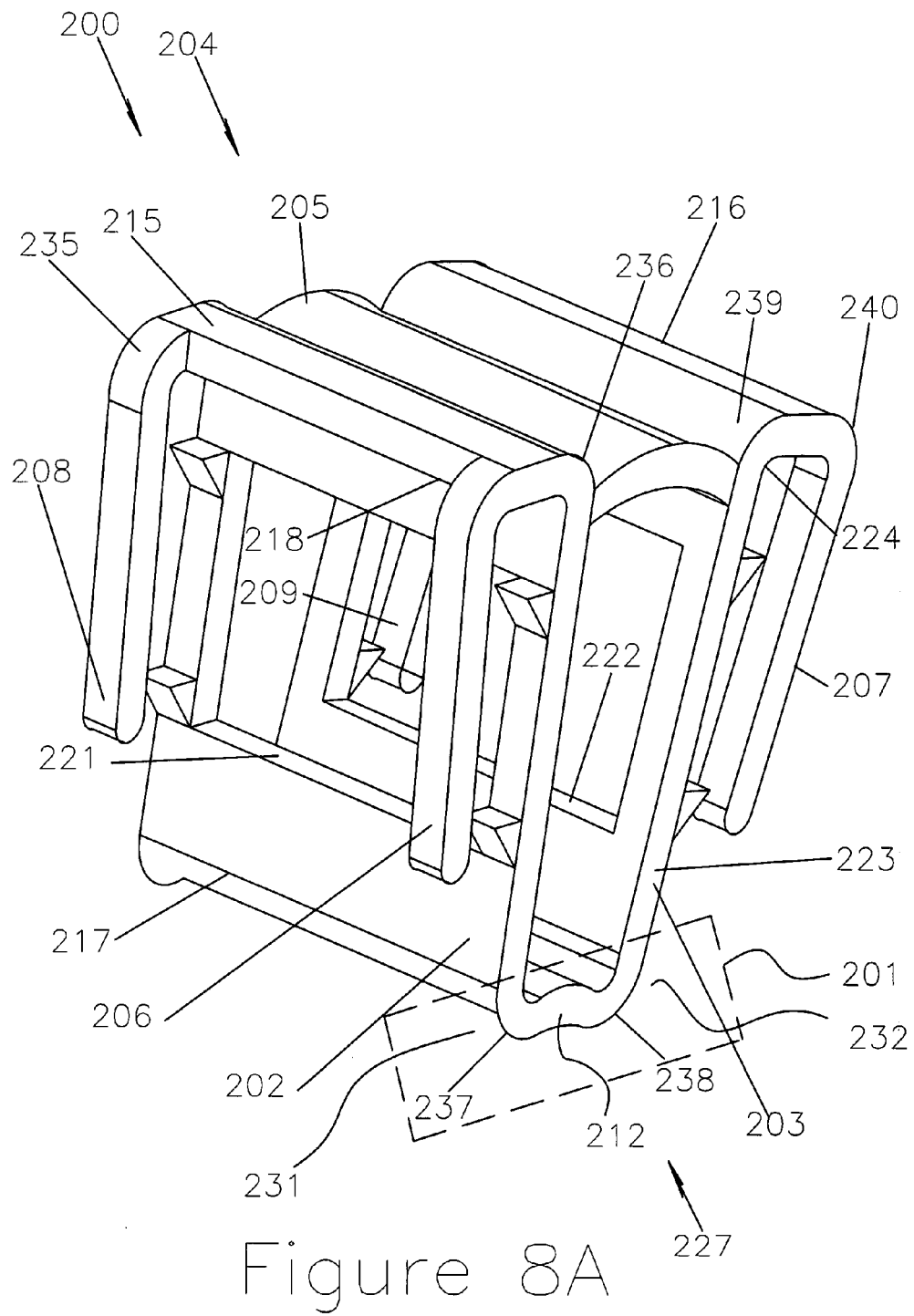
FIG. 8A provides a perspective view of an inter-vertebral cage in a first shape according to a second embodiment.
Figure 8B:
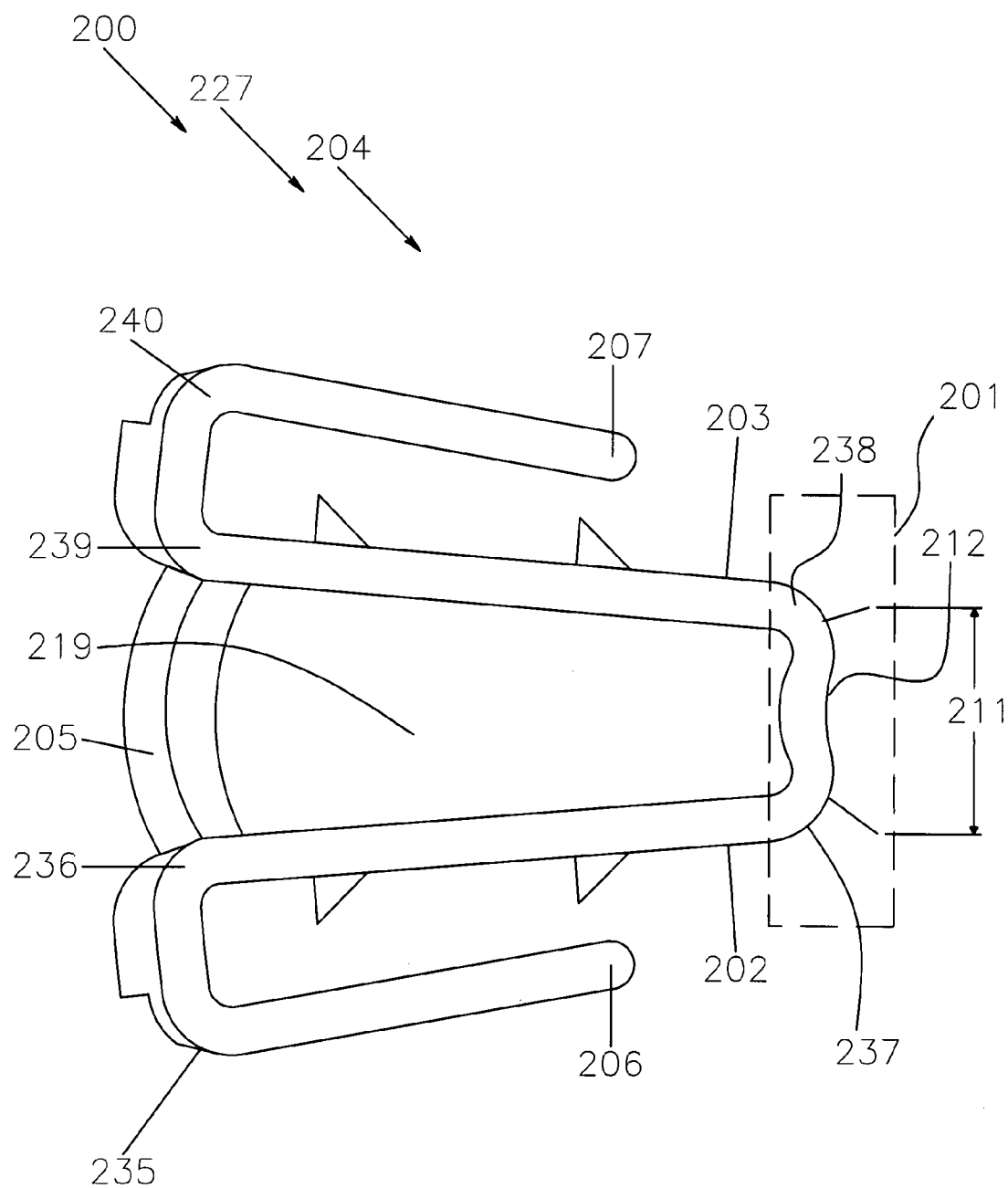
FIG. 8B provides a front view of the inter-vertebral cage in the first shape according to the second embodiment.
Figure 8C:
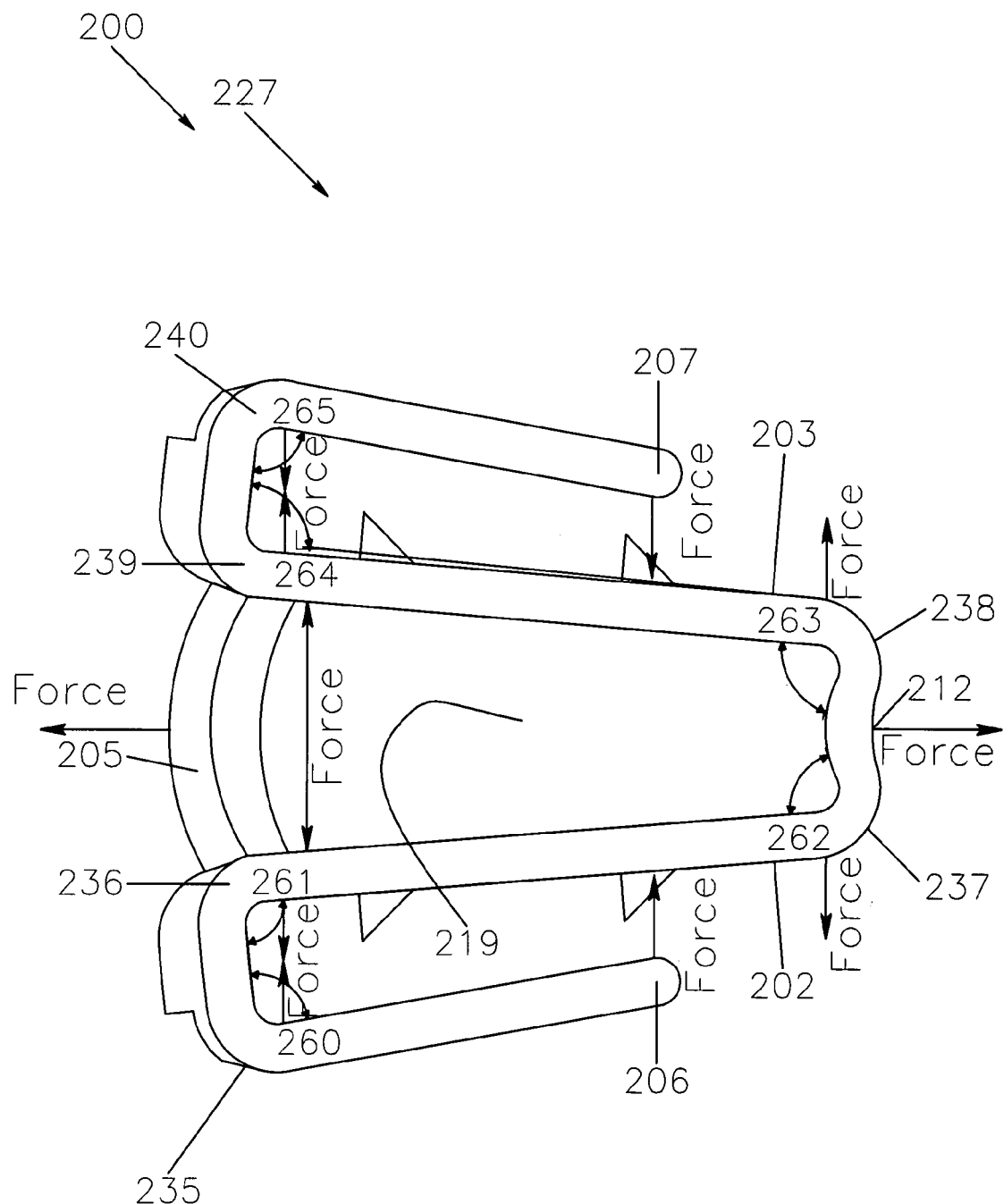
FIG. 8C provides a front view of the inter-vertebral cage in the first shape according to the second embodiment.
Figure 9A:
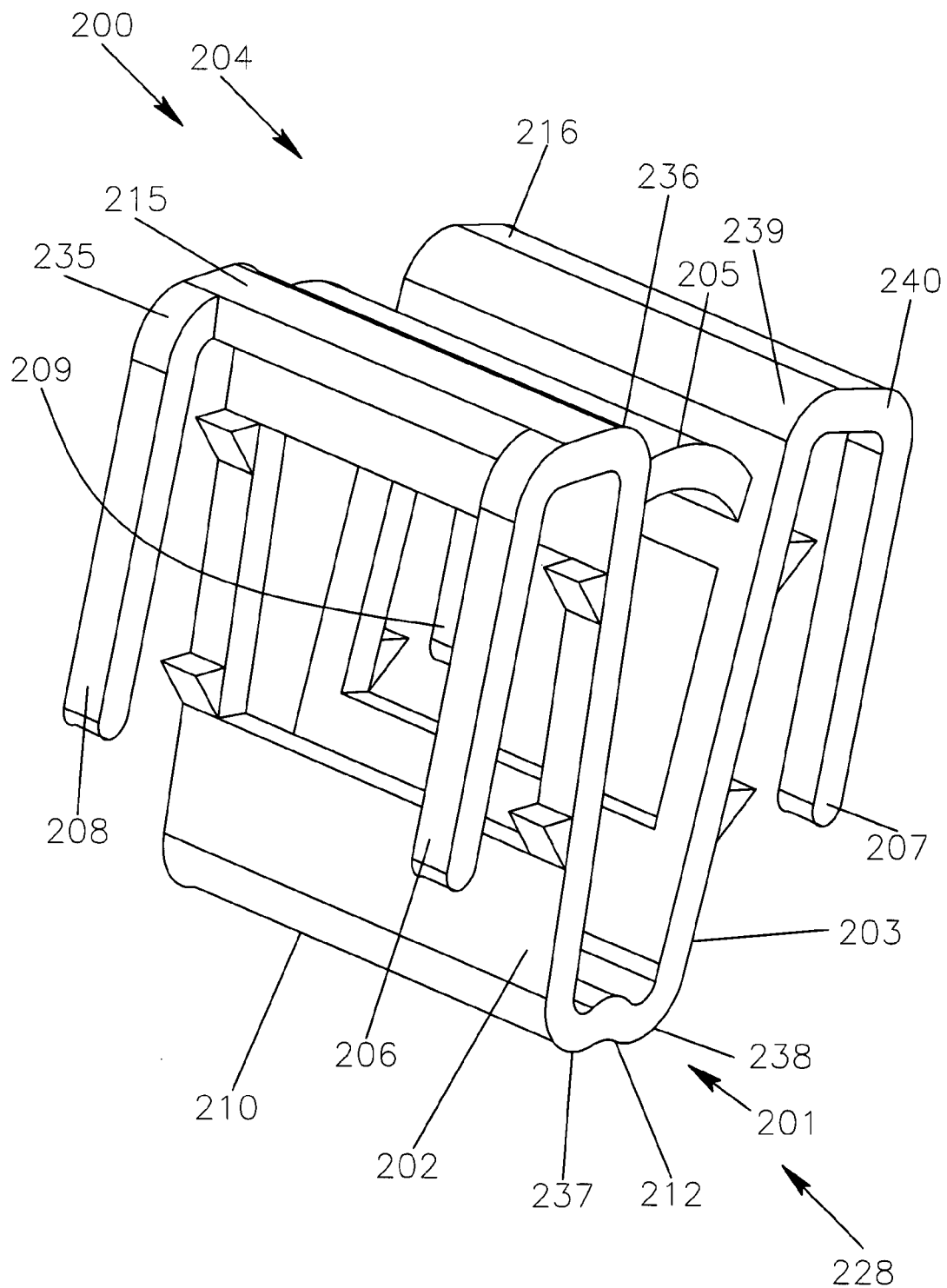
FIG. 9A provides a perspective view of the inter-vertebral cage in a second shape according to the second embodiment.
Figure 9B:
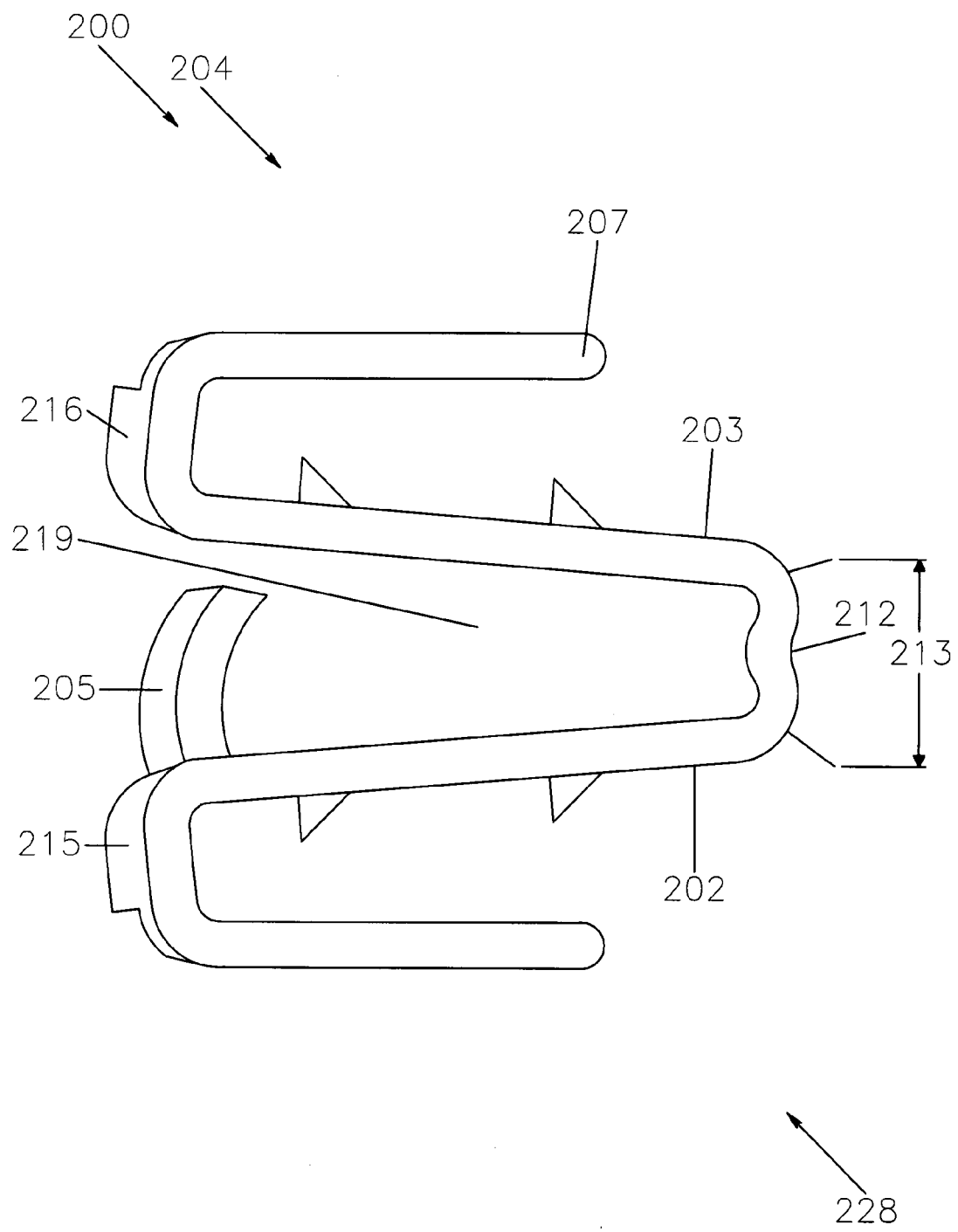
FIG. 9B provides a front view of the inter-vertebral cage in the second shape according to the second embodiment.

The inter-vertebral cage 192 is also formed from a shape memory alloy, and accordingly, also moves from a second shape 128 to a first shape 127, or any point therebetween, in similar fashion to the inter-vertebral cage 100. FIGS. 6A and 6B provide illustrations of the inter-vertebral cage 192 in the first shape 127, and FIGS. 7A-7B provide an illustration of the inter-vertebral cage 192 in a deformed or second shape 128. Upon the transformation of the inter-vertebral cage 192 from the second shape 128 to the first shape 127, forces are created as shown in FIG. 6C. Operation of the inter-vertebral cage 192 is substantially identical to the inter-vertebral cage 100, however in the case of the inter-vertebral cage 192, four legs are disposed within a first and second vertebrae, and energy must also be applied to the additional legs 193 and 194. The surgeon must further identify a third location in the first vertebra 180, and a fourth location in the second vertebra 181, at a spacing complementary to the four legs 106, 107, 193, and 194 of the inter-vertebral cage 192. All other aspects of the inter-vertebral cage 192 are obvious to one of ordinary skill in the art when compared to the inter-vertebral cage 100, and therefore, will not be further described.

In a second embodiment, an inter-vertebral cage 200 is similar in function to the inter-vertebral cage 192, however the inter-vertebral cage 200 includes a vertebrae distraction function. The inter-vertebral cage 200 is similarly constructed from a shape memory alloy, and therefore, may be returned to any point up to an original shape with the application of energy. As shown in FIGS. 8A-8B and 9A-9B, the inter-vertebral cage 200 includes a body 204 having a spacing member 201, a first engagement plate 202, and a second engagement plate 203. The spacing member 201 includes an extension section 212, a bend 237, and a bend 238. The extension section 212, in a first shape 227, includes a width 211, and, in a second shape 228, a width 213.

The first engagement plate 202 includes a first end 217 in communication with a first end 231 of the spacing member 201, and a second end 218 in communication with a first stop 215. The second engagement plate 203 includes a first end 223 that is in communication with a second end 232 of the spacing member 201, and a second end 224 that is in communication with a second stop 216. The first and second stops 215 and 216 are substantially planar in shape, and extend the entire length of the second ends 218 and 224 of the first and second engagement plates 202 and 203. The first engagement plate 202 includes a first aperture 221 substantially identical to that of the first embodiment, and the second engagement plate 203 includes a second aperture 222 substantially identical to that of the first embodiment.

This second embodiment includes a plurality of legs extending from the stops 215 and 216. Illustratively, in this particular example, a first leg 206, a second leg 207, a third leg 208, and a fourth leg 209 are utilized for securing the inter-vertebral cage 200 to bones. In this second embodiment, the first leg 206 and the third leg 208 are disposed on extreme ends of the first stop 215, and the second and fourth legs 207 and 209 are disposed on extreme ends of the second stop 216, in similar fashion to the inter-vertebral cage 192. While this second embodiment has been shown with the inter-vertebral cage 200 having four legs, one of ordinary skill in the art will recognize that fewer or more legs may be utilized as necessary to adapt to in vivo conditions.

The inter-vertebral cage 200 includes a bend 235, a bend 236, a bend 239, and a bend 240, as shown in the first embodiment. The bends 235 through 240 move through a range of angles bordered by an original or first shape 227, and a deformed or second shape 228, in similar fashion to the first embodiment.

The inter-vertebral cage 200 further includes a closeout 205 attached to the first engagement plate 202. In this embodiment, the closeout 205 is extended downward slightly in the second shape 228, and extends towards the second engagement plate 203 upon the application of energy. Upon full extension of the closeout 205, and the contraction of the bends 237-238, the closeout 205 is in contact with the second engagement plate 203, thereby providing load bearing support between the first engagement plate 202 and the second engagement plate 203.

The extension section 212 provides the capability to increase the width 213 associated with the second shape 228 to the width 211 associated with the first shape 227. In this second embodiment, the extension section 212 is a curvature formed into the shape memory material. The curvature flattens out upon the application of energy to the body 204. As such, the bend 237 and the bend 238 move away from each other. The extension section 212 may be flattened out to any point along the transformation from the deformed position to the original position, as previously disclosed. While this embodiment has been shown with a single extension section 212, one of ordinary skill in the art will recognize that multiple extension sections may be utilized to create increased displacements. Additionally, the amount of displacement for a given extension section may be altered by varying the radius, and or thickness of the extension section, as well as its form.

In a second embodiment of the spacing member 201, the spacing member 201 includes a third engagement surface 210 with "S" or "Z" shaped extension members that run from bend 237 to 238. This member is deformed so that it is a straight member in its first shape and "S" or "Z" shaped in its second shape. When placed into the bone and heated the extension member changes back to a straight member, and causes the extension section 212 to increase in length from 213 to 211.

The feature of lengthening the spacing member 201 and adjusting the closeout 205 allows the implant to be used to change the relative angles and positions of the bones. Through partial heat activation of the extension section 212 the bone angle can be set.

Figure 10:
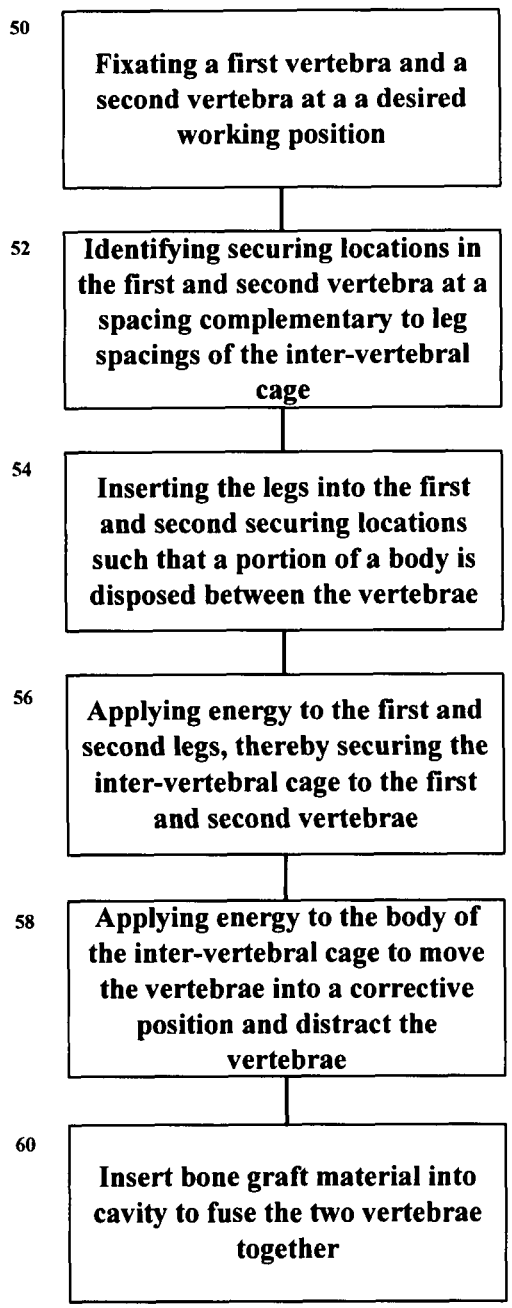
FIG. 10 provides a flowchart illustrating the method steps for utilizing the inter-vertebral cage according to the second embodiment.

FIG. 10 provides a method flowchart illustrating the steps associated with utilizing the inter-vertebral cage 200 to move a first and a second vertebra 280 and 281 to a corrective position. The method shown in FIG. 10 is similar to the method of FIG. 3. However, the method of FIG. 10 provides the ability to separate and lift the first vertebra 280 from the second vertebra 281. As shown in step 50 of the method flowchart, a surgeon fixates a first vertebra 280 and a second vertebra 281 at a desired working position. The process continues with step 52, wherein the surgeon must identify securing locations in the first and second vertebrae 280-281, at a spacing complementary to leg spacings 206-209 of the inter-vertebral cage 200. Step 54 provides for inserting the legs 206-209 of the inter-vertebral cage 200 into the securing locations, such that the engagement plates 202 and 203 and the spacing member 201 of the inter-vertebral cage 200 are disposed between the vertebrae 280 and 281. Upon insertion, the surgeon moves to step 56, wherein energy is applied to the legs 206-209 of the inter-vertebral cage 200, thereby securing the inter-vertebral cage 200 to the first and second vertebrae 280 and 281. The process continues with step 58, wherein energy is applied to the body 204 of the inter-vertebral cage 200, thereby moving the first and second vertebrae 280 and 281 into a desired corrective position, locking the closeout 205, and further distracting the first vertebra 280 and the second vertebra 281 by moving the extension feature 212 from the width 213 to width 211. The surgeon may then insert bone graft material into the cavity 219, thereby promoting the fusion of the first vertebra 280 and the second vertebra 281, step 60.

Figure 11A:
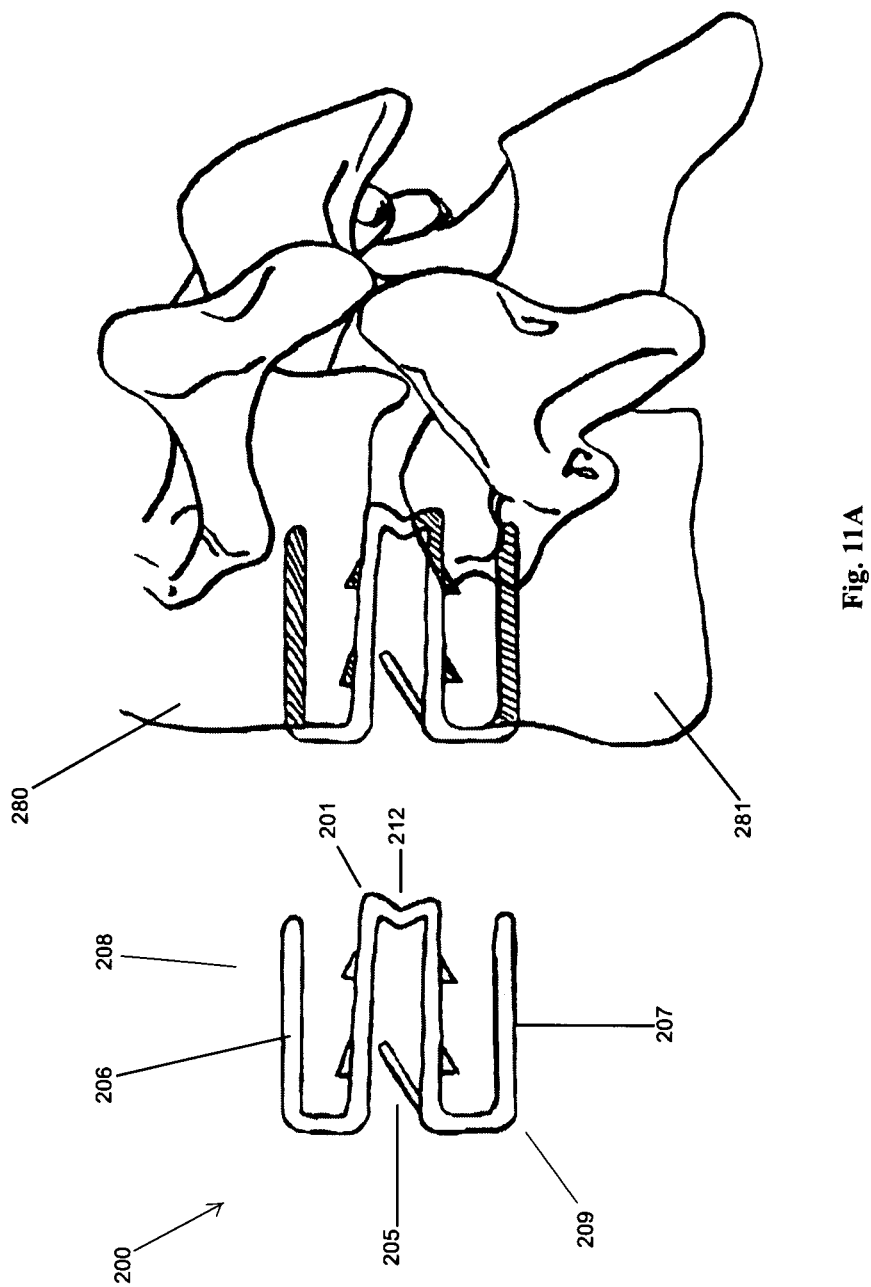
FIG. 11A provides a partial section view of the inter-vertebral cage in a second shape according to the second embodiment.
Figure 11B:
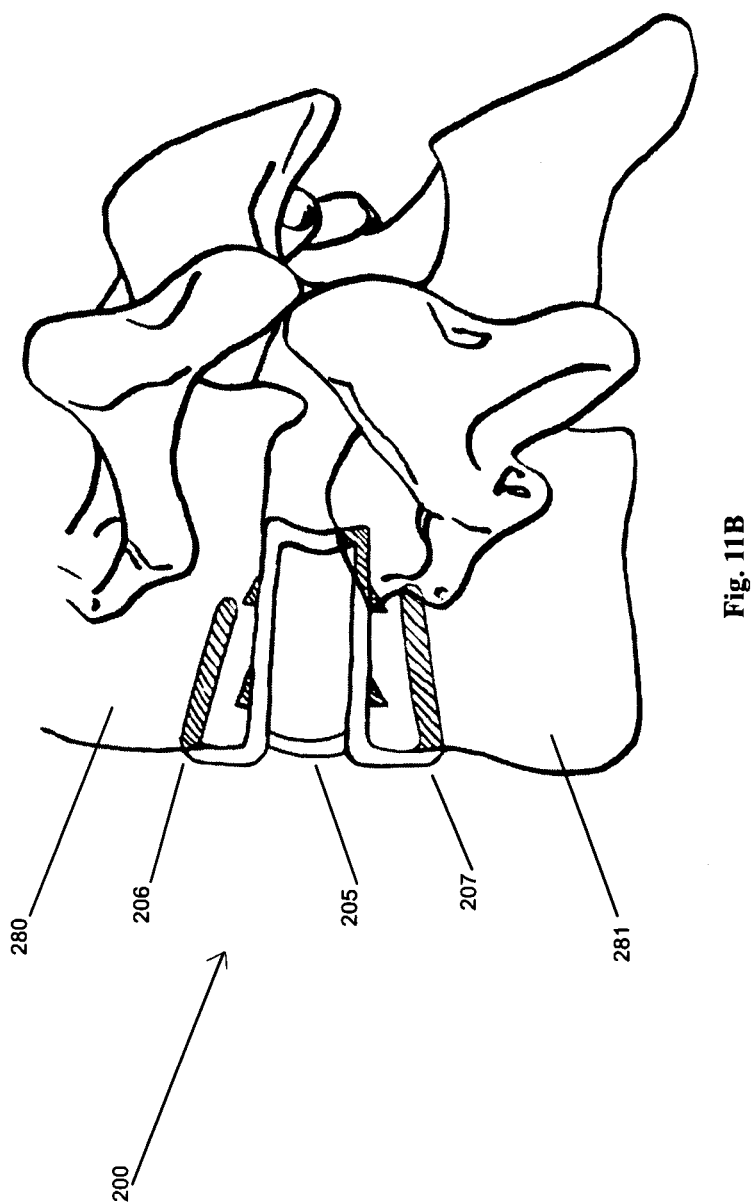
FIG. 11B provides a partial section view of the inter-vertebral cage in a first shape in an installed position according to the second embodiment.

As shown in FIG. 11A, the legs 206-209 of a inter-vertebral cage 200, in a deformed position, are inserted into the first vertebra 280 and the second vertebra 281, such that the engagement surfaces 145 through 150, as described in the first embodiment, contact the first and second vertebra 280 and 281. Upon full insertion, energy is applied to the legs 206-209, such that the legs 206-209 move toward the engagement plates 202-203, thereby securing the inter-vertebral cage 200 to the each respective vertebra 280 or 281. Upon the application of energy to the body 204, the closeout 205 extends toward the second engagement plate 203, and the bends 237 and 238 contract, thereby moving the engagement plates 202 and 203 closer together. When the second engagement plate 203 contacts the closeout 205, the vertebrae 280 and 281 are aligned in the desired corrective position, and the closeout 205 provides support in the vertical direction. Upon further application of energy, the extendable feature 212 of the spacing member 201 flattens out to provide separation between the first and second vertebra 280 and 281 and set the curvature of the spinal vertebral bodies, as shown in FIG. 11B.

Once the first and second vertebrae 280 and 281 are in the desired corrective position, the surgeon inserts bone graft material into the cavity 219, such that the bone graft material unites with the first and second vertebrae 280 and 281 through the first and second apertures 221-222. Upon bone fusion, the graft material and the first and second vertebrae 280 and 281 become a single unit.

Figure 12A:
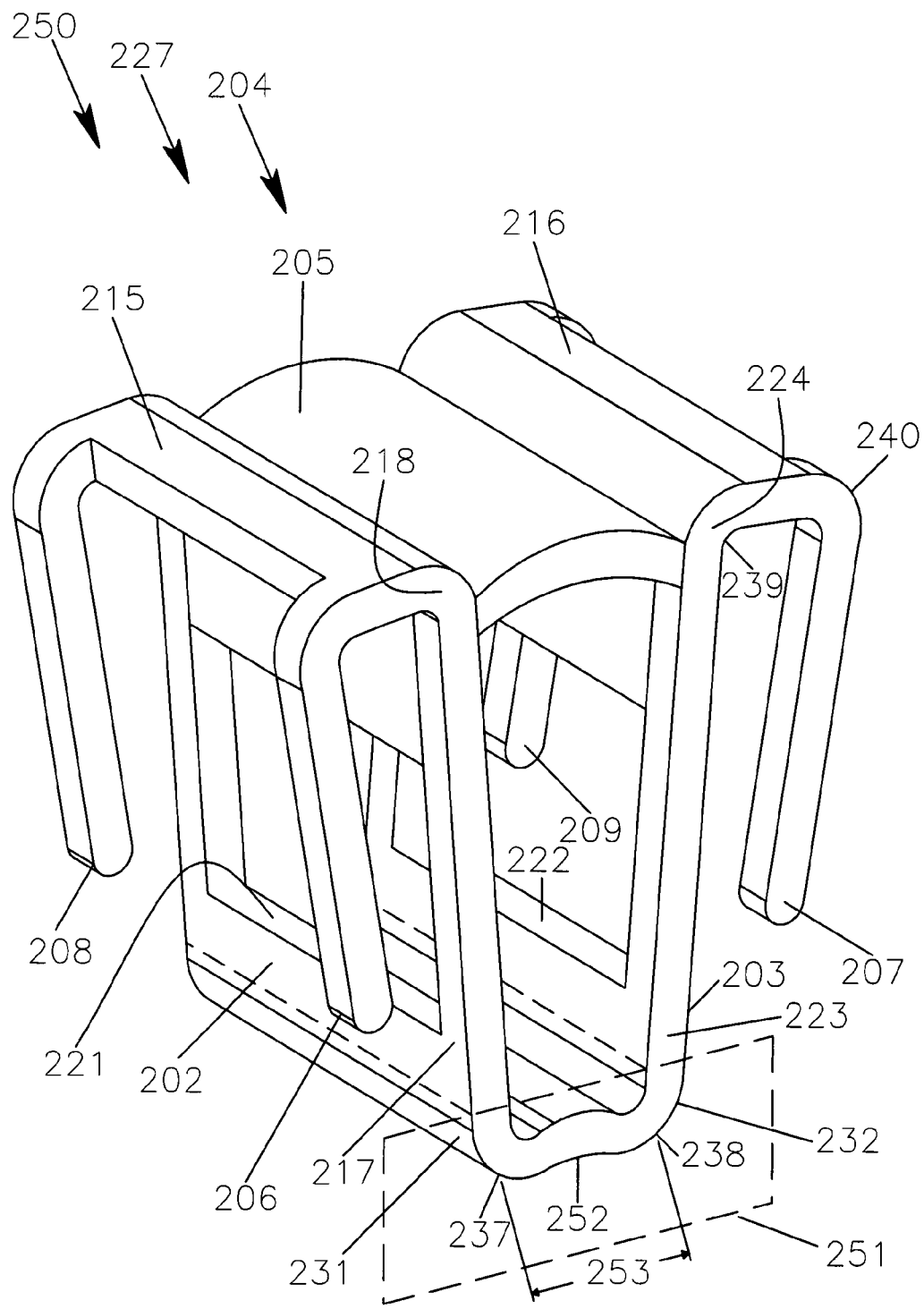
FIG. 12A provides a perspective view of an inter-vertebral cage in a first shape according to an extension of the second embodiment.
Figure 12B:
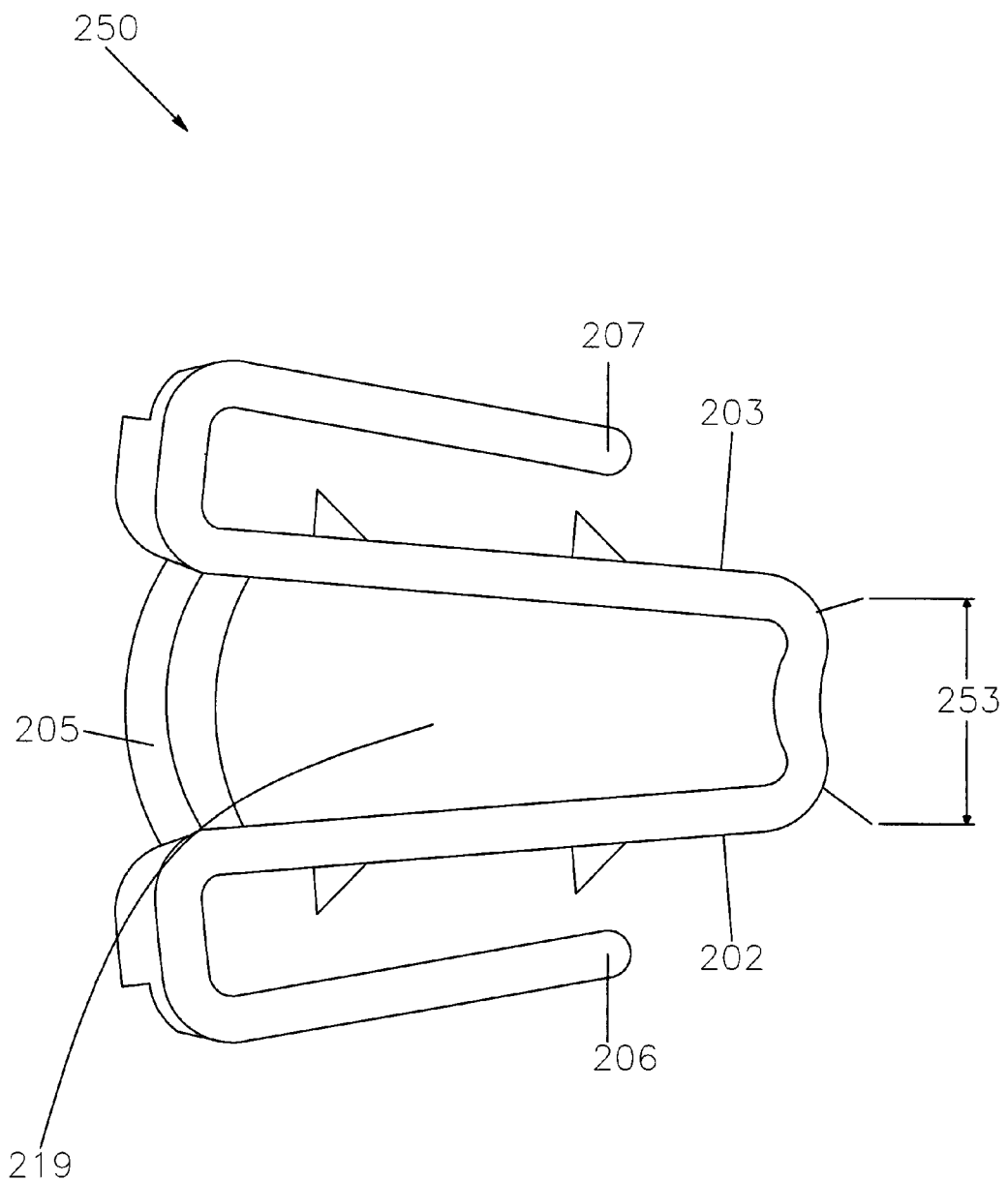
FIG. 12B provides a front view of the inter-vertebral cage in the first shape according to the extension of the second embodiment.
Figure 12C:
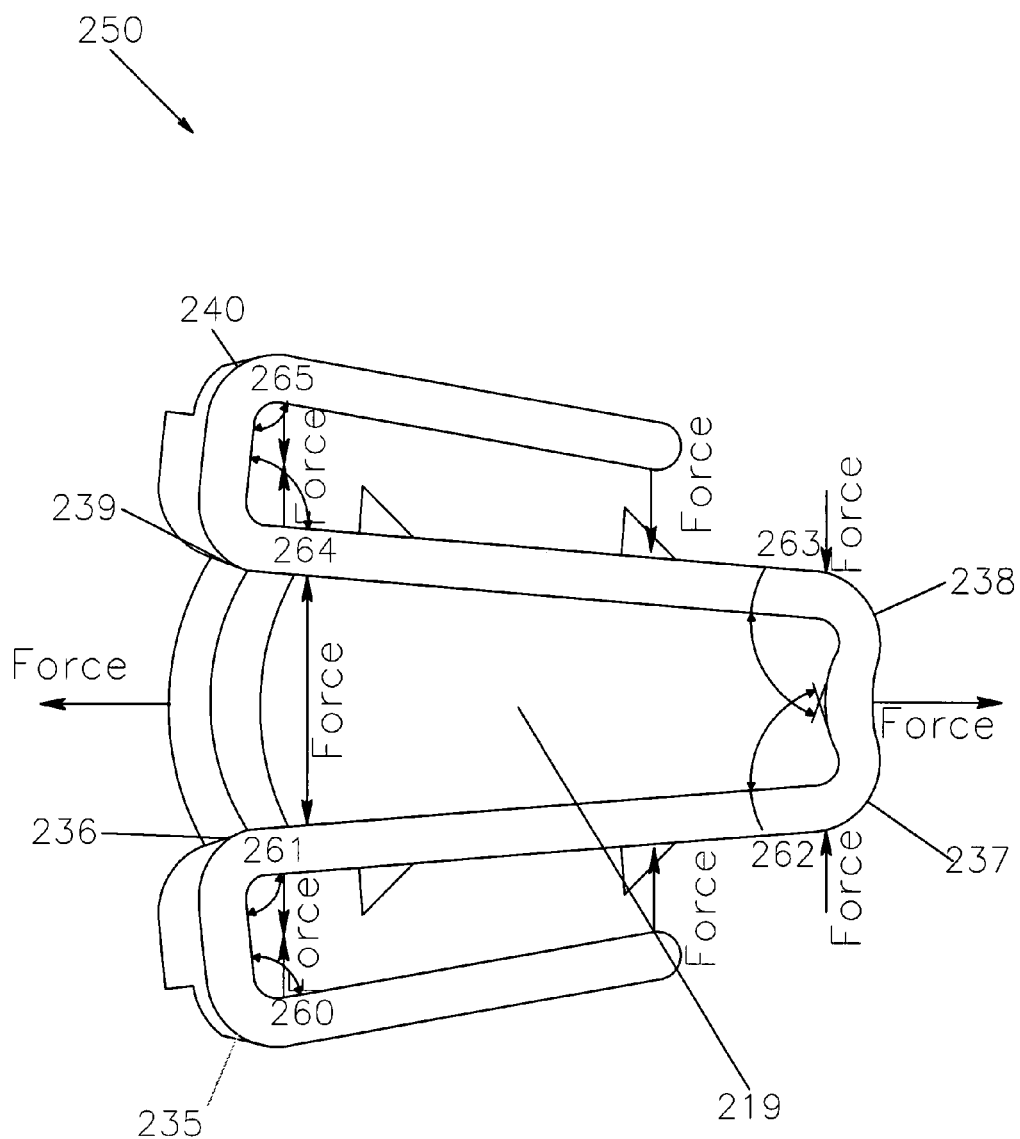
FIG. 12C provides a front view of the inter-vertebral cage in the first shape according to the extension of the second embodiment.
Figure 13A:
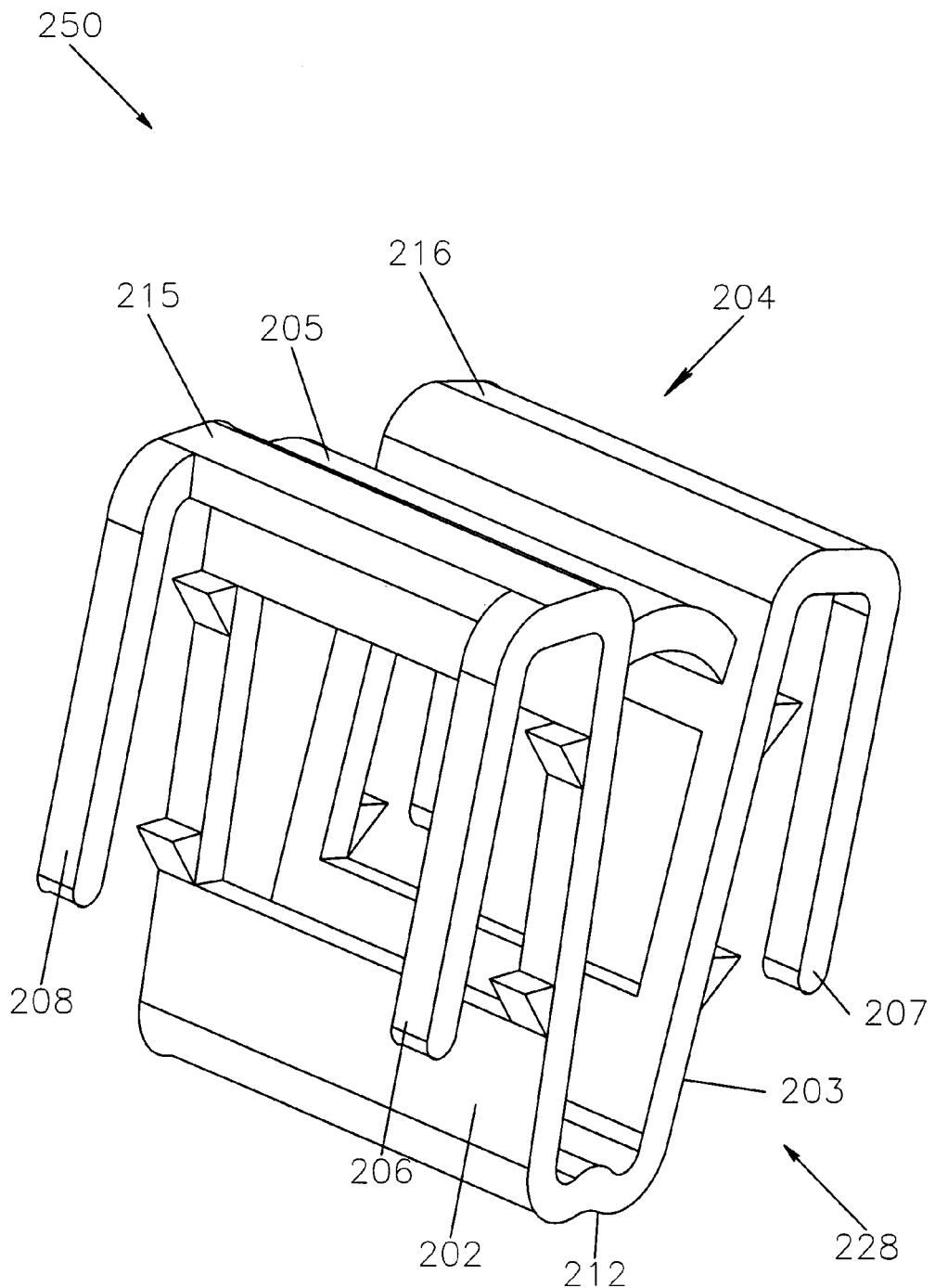
FIG. 13A provides perspective view of the inter-vertebral cage in a second shape according to the extension of the second embodiment.
Figure 13B:
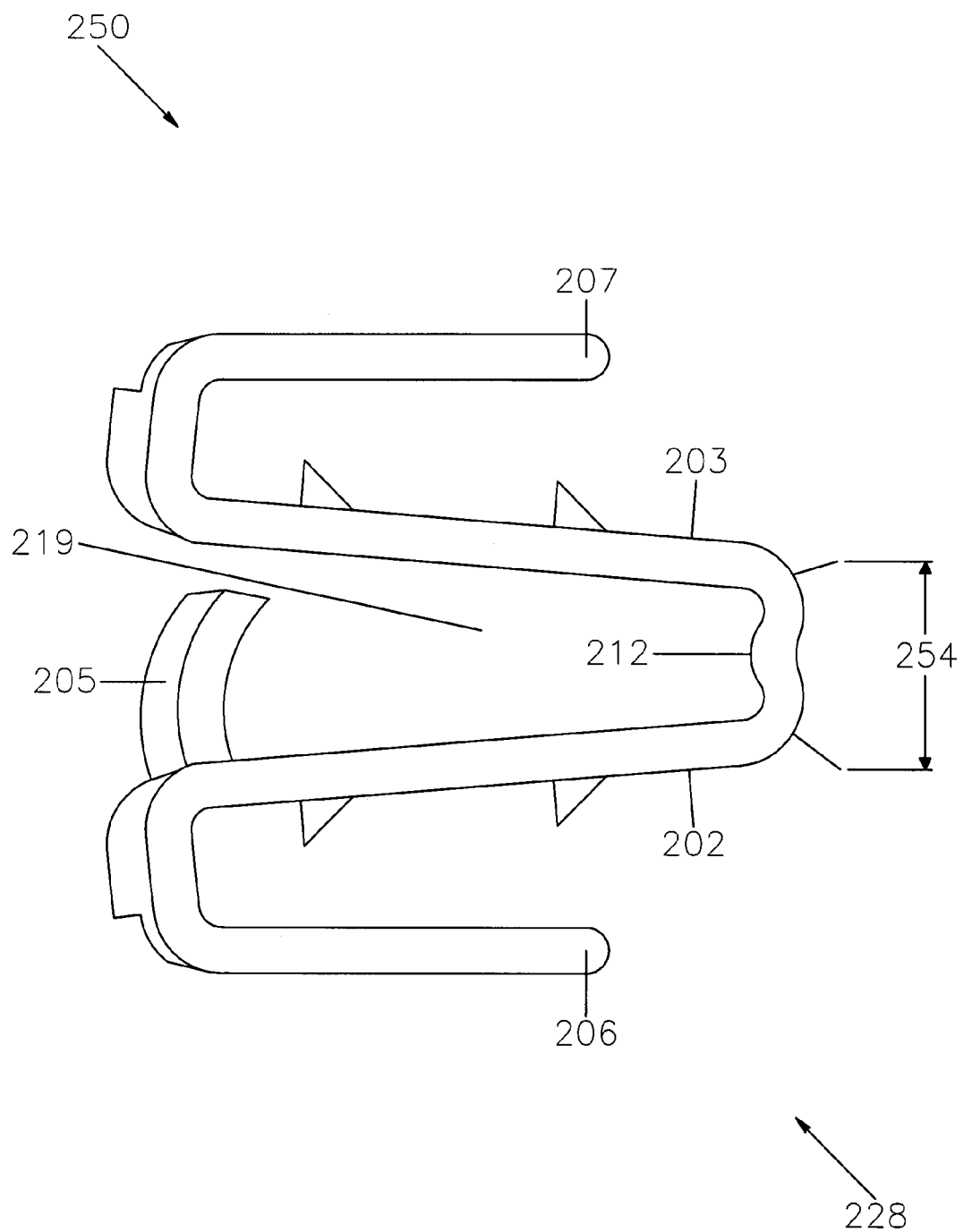
FIG. 13B provides a front view of the inter-vertebral cage in the second shape according to the extension of the second embodiment.

In an extension of the second embodiment, an inter-vertebral cage 250 is similar in design to the inter-vertebral cage 200, however the inter-vertebral cage 250 includes a spacing member 251 providing a contraction function instead of an extension function, as shown in FIGS. 12A-12C. Accordingly, like parts have been annotated with like numerals. The inter-vertebral cage 250 is similarly constructed from a shape memory alloy, and therefore, may be returned to any point up to an original shape with the application of energy. The inter-vertebral cage 250 includes a body 204 having a spacing member 251, a first engagement plate 202, and a second engagement plate 203. The spacing member 251 includes a contraction section 252, a bend 237, and a bend 238. The contraction section 252, in a first shape 227, includes a width 253, an, in a second shape 228, as shown in FIGS. 13A-13B, a width 254. All other aspects and components of the inter-vertebral cage 250 are identical to those presented in the second embodiment, and therefore, will not be further described.

The contraction section 252 provides the capability to decrease the width 254 associated with the second shape 227 to the width 253 associated with the first shape 227. In this extension of the second embodiment, the contraction section 252 is a curvature formed in the shape memory material. The curved portion constricts upon the application of energy to the body 204. As such the bends 237 and 238 move toward each other. The contraction section 252 may be constricted to any point along the transformation from the deformed position to the original position, as previously disclosed. While this embodiment has been shown with a single contraction section, one of ordinary skill in the art will recognize that multiple contraction sections may be utilized to create increased contractions. One of ordinary skill in the art will further recognize that the inclusion of both a contraction section 252 and an extension section 212 of the second embodiment in a spacing member is within the scope of this invention.

Figure 14:
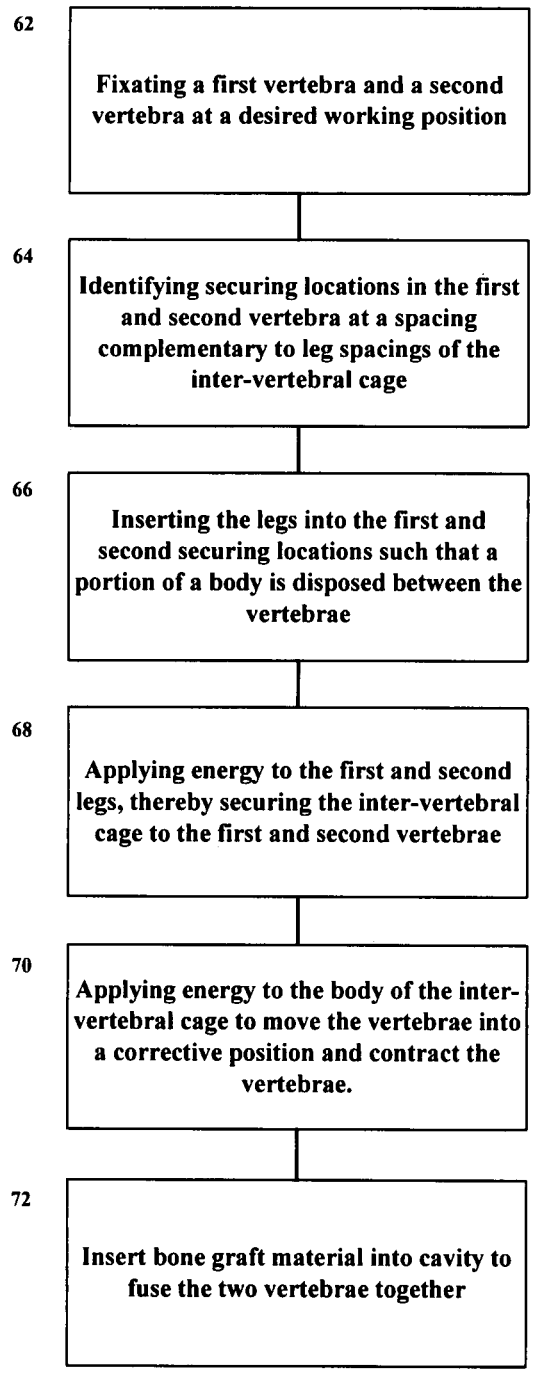
FIG. 14 provides a method flowchart illustrating the method steps for utilizing the inter-vertebral cage according to the extension of the second embodiment.

FIG. 14 provides a method flowchart illustrating the steps associated with utilizing the inter-vertebral cage 250 to move a first and a second vertebra 280 and 281 to a corrective position. The method shown in FIG. 14 is similar to the method of FIG. 10. However, the method of FIG. 14 provides the ability to contract the first vertebra 280 and the second vertebra 281. As shown in step 62 of the method flowchart, a surgeon fixates a first vertebra 280 and a second vertebra 281 at a desired working position. The process continues with step 64, wherein the surgeon must identify securing locations in the first and second vertebrae 280-281, at a spacing complementary to leg spacings 206-209 of the inter-vertebral cage 250. Step 66 provides for inserting the legs 206-209 of the inter-vertebral cage 250 into the securing locations, such that the engagement plates 202 and 203 and the spacing member 251 of the inter-vertebral cage 250 are disposed between the vertebrae 280 and 281. Upon insertion, the surgeon moves to step 68, wherein energy is applied to the legs 206-209 of the inter-vertebral cage 250, thereby securing the inter-vertebral cage 250 to the first and second vertebrae 280 and 281. The process continues with step 70, wherein energy is applied to the body 204 of the inter-vertebral cage 250, thereby moving the first and second vertebrae 280 and 281 into a desired corrective position, and further contracting the first vertebra 280 and the second vertebra 281 by constricting the contraction section 252 from the width 254 to width 253. The surgeon may then insert bone graft material into the cavity 219, thereby promoting the fusion of the first vertebra 280 and the second vertebra 281, step 72. While the method of implanting inter-vertebral cage 250 has been presented, one of ordinary skill in the art will recognize that the sequence of steps may be changed to meet a specific clinical need.

Upon the application of energy to the body 204 and legs 206-209 of the inter-vertebral cage 250, forces are generated as shown in FIG. 12C. As the legs 206-209 move closer to the first and second engagement plates 202-203, compressive forces are created between the legs 206-209 and the engagement plates 202-203. Compressive forces are created between the first and second engagement plates 202-203 when the engagement plates move together. Additionally, compressive forces are created between the first and second engagement plates 202 and 203 when the contraction section 252 constricts.

Figure 15B:
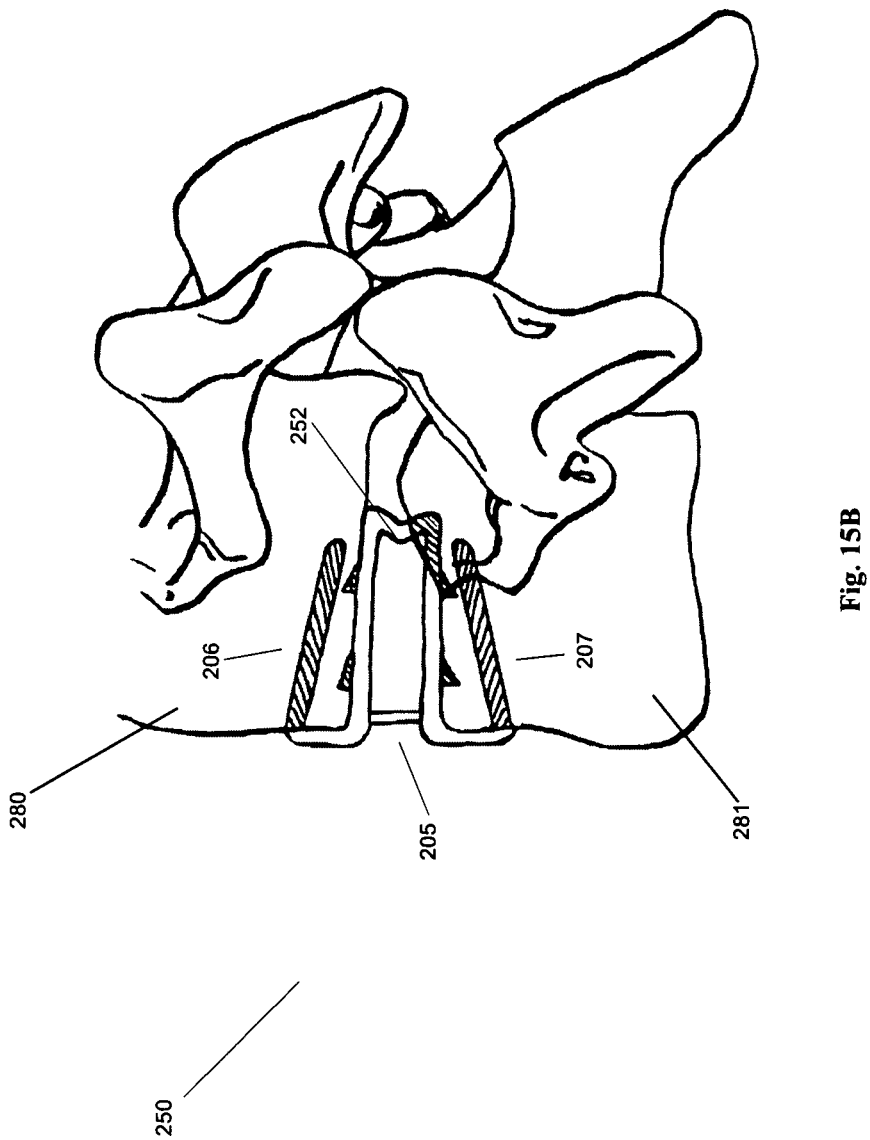
FIG. 15B provides a partial section view of the inter-vertebral cage in a first shape after contraction according to the second embodiment.

As shown in FIG. 15A, the legs 206-209 of a inter-vertebral cage 250, in a deformed position, are inserted into the first vertebra 280 and the second vertebra 281, such that the engagement surfaces 145 through 150, as described in the first embodiment, contact the first and second vertebra 280 and 281. Upon full insertion, energy is applied to the legs 206-209, such that the legs 206-209 move toward the engagement plates 202-203, thereby securing the inter-vertebral cage 250 to the each respective vertebra 280 or 281, as shown in FIG. 15B. Upon the application of energy to the body 204, the closeout 205 extends toward the second engagement plate 203, and the bends 237 and 238 contract, thereby moving the engagement plates 202 and 203 closer together. When the second engagement plate 203 contacts the closeout 205, the vertebrae 280 and 281 are aligned in the desired corrective position, and the closeout 205 provides support in the vertical direction. Upon further application of energy, the contraction section 252 of the spacing member 251 constricts to bring the first and second vertebra 280 and 281 closer together, as shown in FIG. 15B.

Once the first and second vertebrae 280 and 281 are in the desired corrective position, the surgeon inserts bone graft material into the cavity 219, such that the bone graft material unites with the first and second vertebrae 280 and 281 through the first and second apertures 221-222. Upon bone fusion, the graft material and the first and second vertebrae 280 and 281 become a single unit.

Figure 16A:
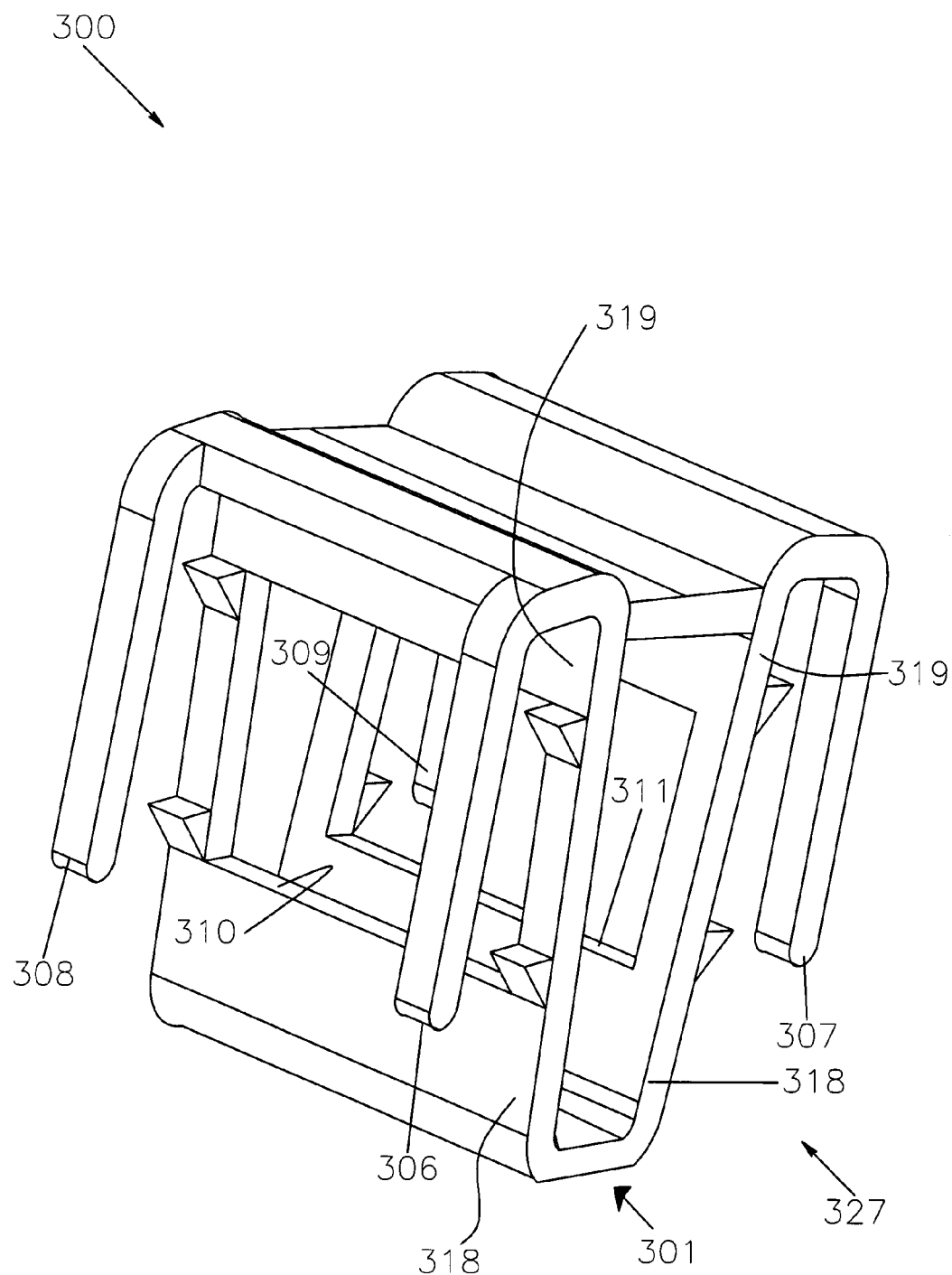
FIG. 16A provides perspective view of the inter-vertebral cage according to a third embodiment.
Figure 16B:
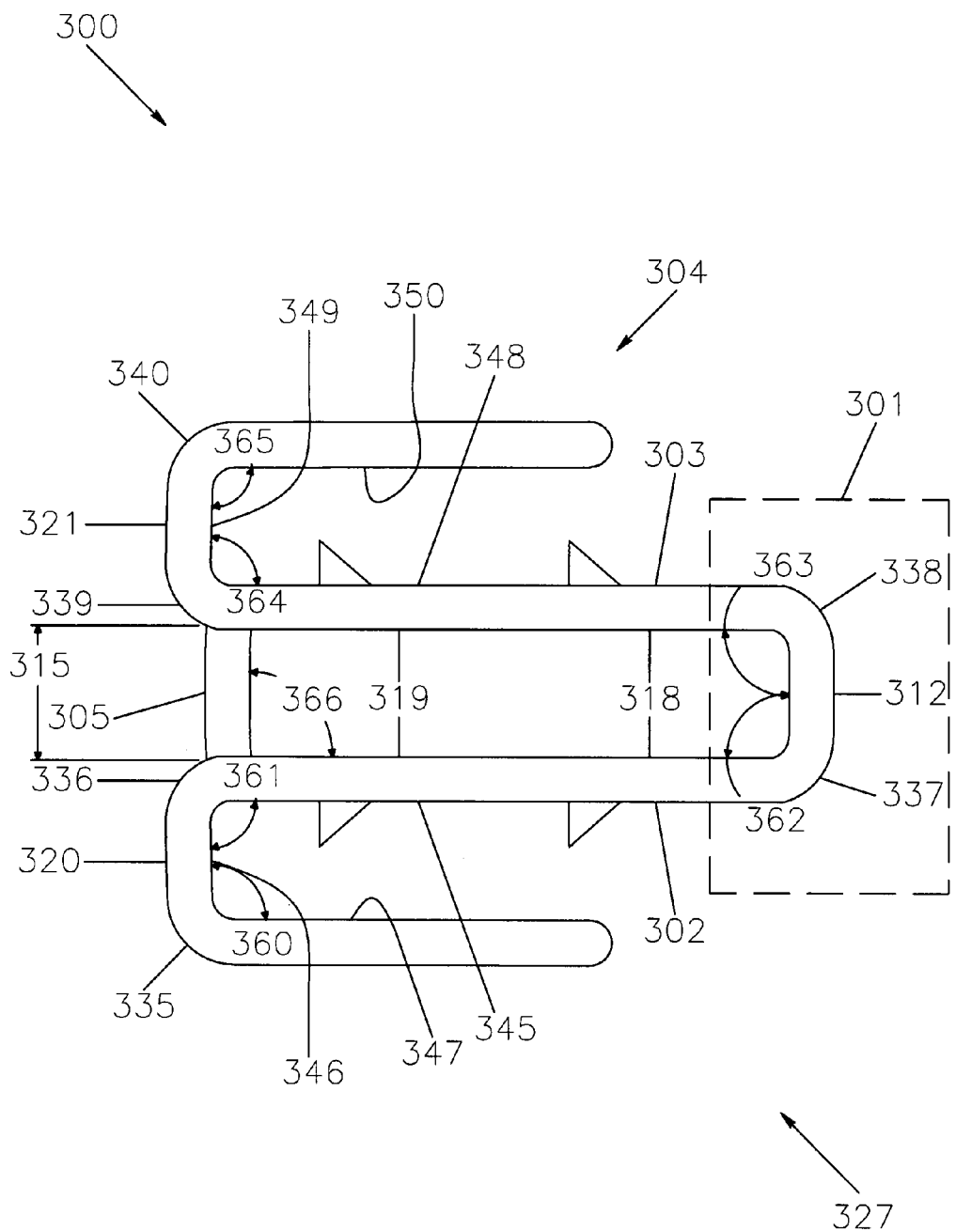
FIG. 16B provides a front view of the inter-vertebral cage in a first shape according to the third embodiment.
Figure 17A:
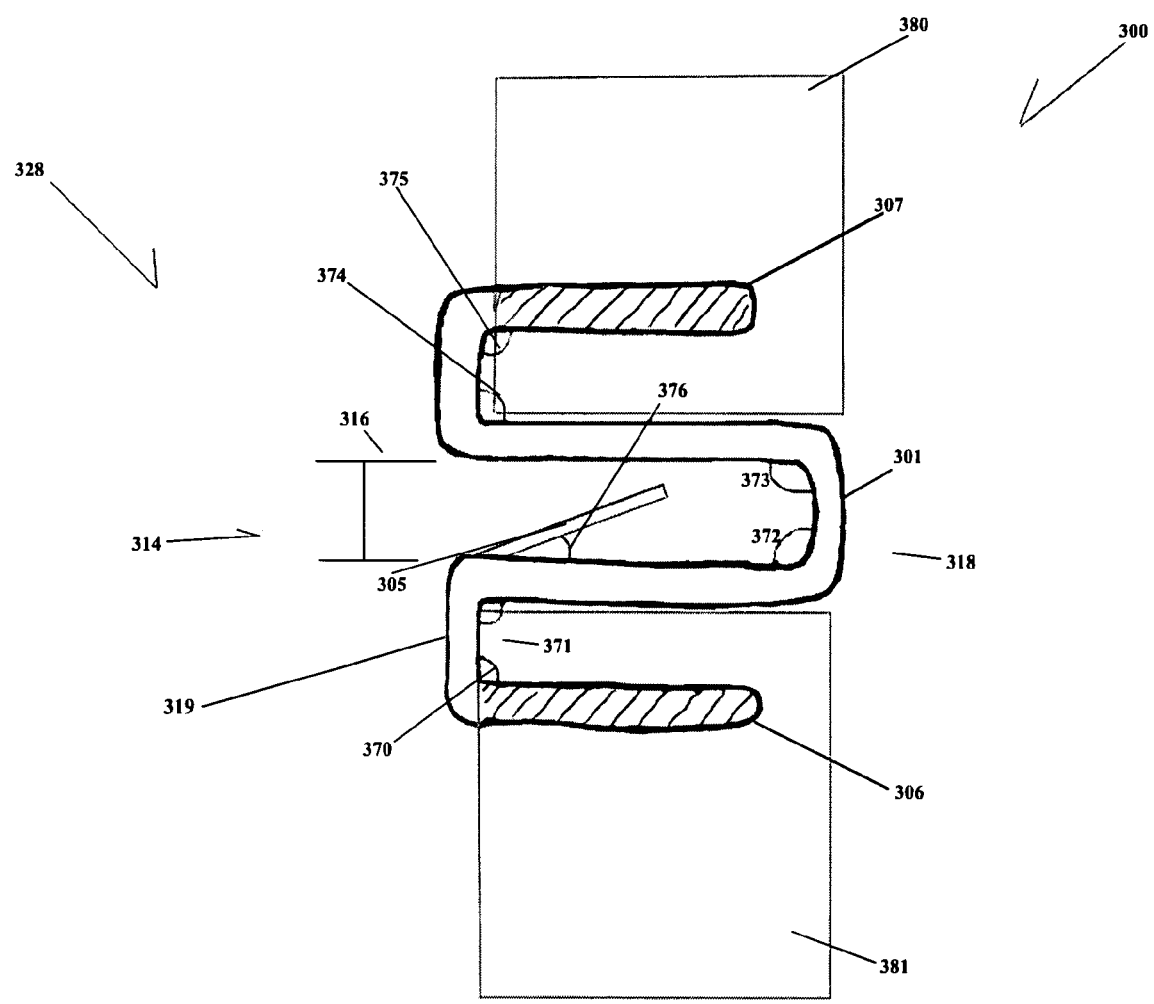
FIG. 17A provides a front view of the inter-vertebral cage in it's second shape in a representation of an improperly curved spine according to the third embodiment.
Figure 17B:
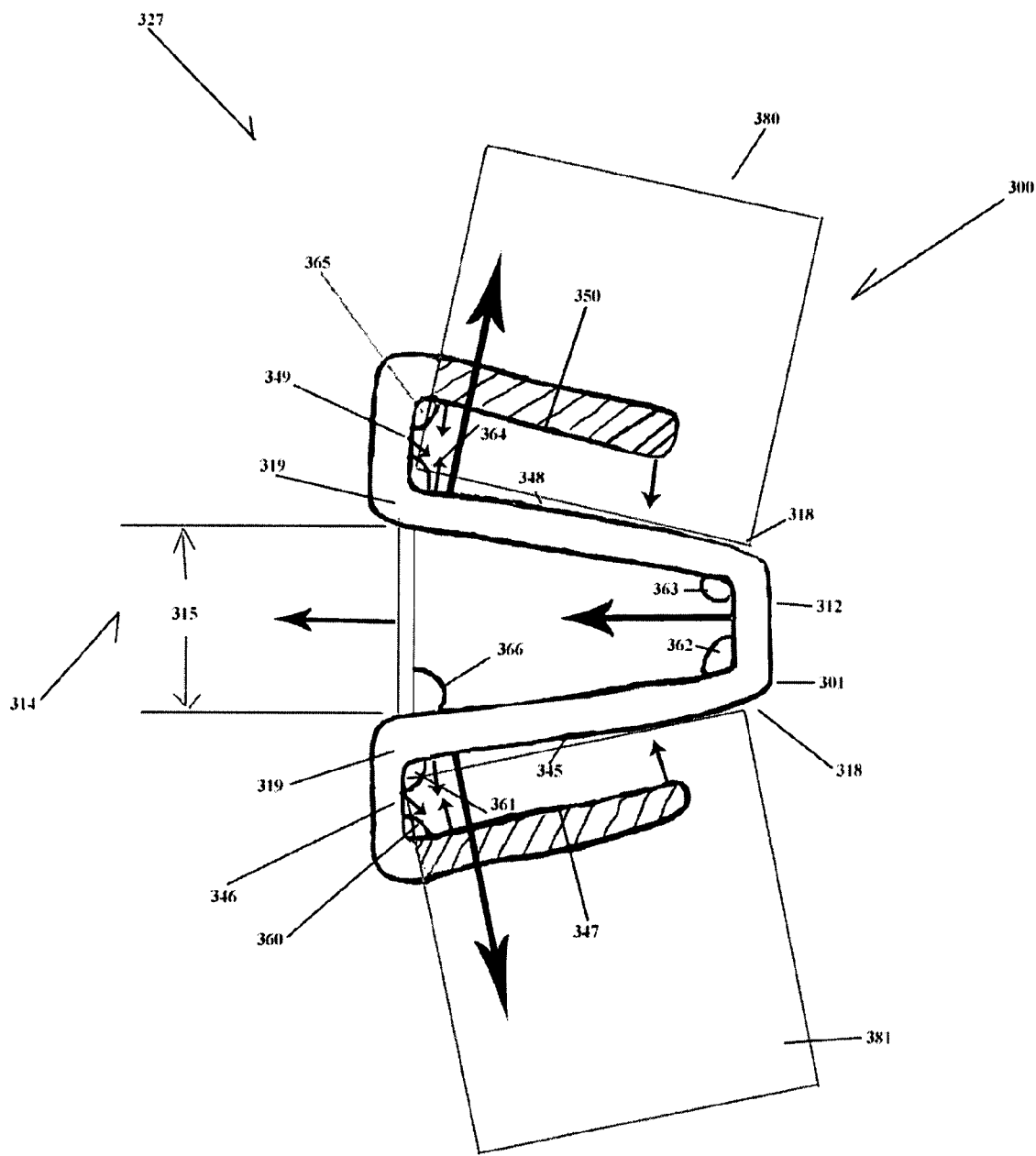
FIG. 17B provides a front view of the inter-vertebral cage in it's first shape where it assumes an expanded position to provide proper curved spine alignment according to the third embodiment.

In a third embodiment, an inter-vertebral cage 300, as shown in FIGS. 16A-16B, is similarly constructed from shape memory material, and, in similar fashion to the first and second embodiments, may move from a second shape 328 to a first shape 327. It should be apparent that the inter-vertebral cage 300 is usable at virtually any point along the transition between the second shape 328 and the first shape 327, as shown in FIGS. 17A-17B. Accordingly, an end-use shape may designate any shape between the second shape 328 and up to and including the first shape 327. The amount of heat energy applied to the deformed shape determines the amount of transition from the second shape 328 to the first shape 327.

As shown in FIGS. 16A-16B, the inter-vertebral cage 300 includes a spacing member 301 disposed between a first engagement plate 302 and a second engagement plate 303. The spacing member 301 includes a planar section 312 disposed between a bend 337 and a bend 338. The inter-vertebral cage 300 further includes a closeout 305 extending from the first engagement plate 302, and legs 306 through 309 disposed on the engagement plates 302 and 303 in similar fashion to the inter-vertebral cage 192. The engagement plates 302 and 303 further include a first end 318 and a second end 319, wherein stops 320 and 321 are disposed on the second ends 319 of the engagement plates 302 and 303. The engagement plates 302 and 303 further include apertures 310 and 311 to aid in bone grafting operations. The inter-vertebral cage 300 further includes bends 335-336 and 339-340, and first through third engagement surfaces 345-350, in similar fashion to the previous embodiments.

In the first shape 327, the second ends of the engagement plates 302 and 303 are disposed at a maximum angle relative to each other, thereby creating a width 315 between the second ends 319 of the engagement plates 302 and 303, as shown in FIG. 17B. In this specific example, the engagement plates 302 is disposed at an angle 362 relative to the planar section 312 of the spacing member 301, and engagement plate 303 is disposed at an angle 363 relative to the planar section 312. In this specific example, each engagement plate 302-303 is disposed at an angle of approximately one hundred and ten degrees relative to the planar section 312 of the inter-vertebral cage 300. While one hundred and ten degrees has been shown, one of ordinary skill in the art will recognize that virtually any angle may be utilized. In similar fashion to the previously disclosed embodiments, the legs 306 through 309 contract towards their respective engagement plates 302 or 303. In this first shape 327, the legs 306-309 are disposed at angle 360 and 365 relative to the stops 320 and 321, and the stops 320 and 321 are disposed at angle 361 and 364 relative to the engagement plates 302 and 303. In this specific example of the first shape 327, the legs 306 through 309 are disposed at an angle of approximately eighty degrees relative to the planar section 312 of the spacing member 301. One of ordinary skill in the art will recognize that this invention is not limited the legs being disposed at approximately eighty degrees relative to the planar section 312.

Additionally, the closeout 305 extends toward the second engagement plate 303 until it contacts the second engagement plate 303. In this example of the first shape 327, the closeout plate 305 is disposed at an angle 366. Specifically, the closeout 305 is disposed substantially parallel to the planar section 312 of the spacing member 301. While the closeout has been shown as being substantially parallel to the planar section 312 of the spacing member 301, one of ordinary skill in the art will recognize that other angles are possible, and should be construed as part of this invention.

In the second shape 328, the inter-vertebral cage 300 is deformed as shown in FIG. 17A, such that bends 337 and 338 of the first shape 327 are contracted to angles 372 and 373, respectively. In this specific example of the second shape 328, the engagement plates 302 and 303 are disposed at an angle of ninety degrees relative to the planar section 312 of the spacing member 301. However, one of ordinary skill in the art will recognize that any angle from the second shape 328 up to an including the first shape 327 may be utilized as an end use shape. The bends 335-336 and 339-340 are similarly extended from their positions associated with the first shape 327. In this second shape, the legs 306-309 are disposed at an angle 370 and 375 relative to the stops 320 and 321. The stops 320 and 321 are disposed at angle 371 and 374, such that the legs 306-309 are disposed substantially perpendicular to the planar section 312 of the spacing member 301, and substantially parallel to each other. In this specific example, the legs are disposed at an angle of substantially ninety degrees relative to the stops 320 and 321, and the stops 320 and 321 are disposed at an angle of substantially ninety degrees relative to the engagement plates 302 and 303. While substantially perpendicular angles have been shown to describe the relationships between the components of the inter-vertebral cage 300, one ordinary skill in the art will recognize that other angles are possible, and should be viewed as part of this invention. One of ordinary skill in the art will further recognize that the use of parallel legs 306-309 is conducive to the impaction of the legs 306-309 into vertebrae or the insertion of the legs into pre-drilled holes; however, other angles may be utilized to address alternative situations, including the insertion of one leg at a time.

Upon the application of energy, the inter-vertebral cage 300 in a deformed or second shape 328 commences to change from the martensitic state to the austenitic state. Upon completion of the austenitic phase change, the inter-vertebral cage 300 has returned to the original or first shape 327. Upon cooling, the inter-vertebral cage 300 retains the original or first shape 327. One of ordinary skill in the art will recognize that upon the transformation of a shape memory alloy to the original shape 327, a force is created, and accordingly, the inter-vertebral cage 300 may be utilized in applications where retaining and residual forces are required.

In this third embodiment, the phase change from the deformed or second shape 328 to the original or first shape 327 creates forces as shown in FIG. 17B. The bend 335 moves from the angle 370 (angle associated with second shape 328) to a more acute angle 360 (acute angle associated with the first shape 327), thereby rotating the first leg 306 and the third leg 308 toward the first engagement plate 302. In a similar fashion, the bend 340 moves from the angle 375 (angle associated with second shape 328) to a more acute angle 365 (acute angle associated with the first shape 327), thereby rotating the second leg 307 and the fourth leg 309 towards the second engagement plate 303. The bend 336 moves from the angle 371

(angle associated with second shape 328) to a smaller angle 361 (associated with the first shape 327). Similarly, the bend 339 moves from the angle 374 (angle associated with second shape 328) to a smaller angle 364 (associated with the first shape 327). Additionally, the bend 337 moves from angle 372 (substantially perpendicular angle associated with second shape 328) to angle 362 (obtuse angle associated with first shape 327). Similarly, the bend 338 moves from the angle 373 (substantially perpendicular angle associated with second shape 328) to angle 363 (obtuse angle associated with first shape 327). Further, the closeout 305 moves from angle 376 (acute angle associated with second shape 328) to the angle 366 (larger angle associated with first shape 327).

In this third embodiment, compressive forces are created between the first engagement surface 345 and the third engagement surface 347. Additionally, compressive forces may be created between the second engagement surface 346 and the third engagement surface 347 as the first leg 306 closes down on material disposed between the first leg 306 and the first engagement plate 302. Compressive forces are also created between the third engagement surface 350 and the first engagement surface 348, and between the second engagement surface 349 and the third engagement surface 350 as the second leg 307 moves towards the second engagement plate 303. Expansive forces are further created by the first engagement plate 302 and the second engagement plate 303 as the bends 337-338 expand to angles 362 and 363, respectively. When the first through fourth legs 306-309 are secured, a thrust component is created as the inter-vertebral cage 300 moves from the first shape 327 to the second shape 328. The thrust force, shown in FIG. 17B, lies perpendicular to the plane of the spacing member 101 and towards the closeout 305. The thrust force is created when the legs 306-309 are pinned, and the first and second engagement plates 302 and 303 move away from each other during the shape change.

Figure 18:
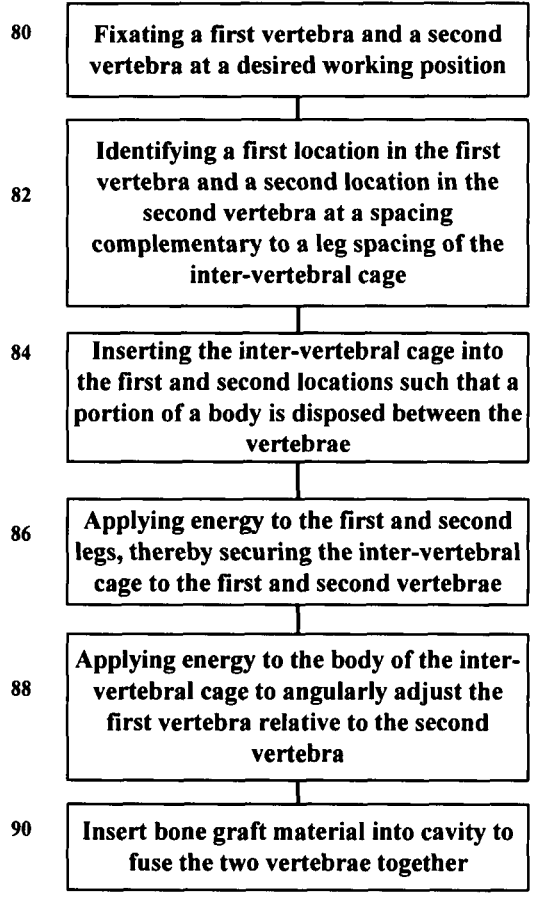
FIG. 18 provides a method flowchart illustrating the method steps for utilizing the inter-vetebral cage to angularly adjust vertebrae according to the third embodiment.

FIG. 18 provides a flowchart illustrating the method steps associated with utilizing the inter-vertebral cage 300 to angularly adjust and fuse two vertebrae together. The process commences with step 80, wherein a surgeon fixates a first vertebra 380 and a second vertebra 381 at a desired working position. The surgeon continues with step 82, wherein a first securing location is identified in the first vertebra 380, and a second securing location is identified in the second vertebra 381 at a spacing complementary to a spacing between the legs 306-309 of the inter-vertebral cage 300. The process continues with step 84, wherein the surgeon inserts the legs 306-309 into the securing locations, such that the first and second engagement plates 302 and 303 are disposed between the first and second vertebrae 380 and 381. In step 86, the surgeon applies energy to the legs 306-309 of the inter-vertebral cage 300, thereby securing the inter-vertebral cage 300 to the first and second vertebrae 380 and 381. The process continues with step 88, wherein the surgeon applies energy to the body 304 of the inter-vertebral cage 300 to angularly adjust the first vertebra 380 relative to the second vertebra 381, and into a desired corrective position. Once the first and second vertebrae 380 and 381 are in the desired corrective position, the surgeon moves to step 90, wherein bone graft material is inserted into the cavity 314, such that the bone graft material unites with the first and second vertebrae 380 and 381 through the first and second apertures 310 and 311. Upon bone fusion, the graft material and the first and second vertebrae 380 and 381 become a single unit.

FIG. 17a provides a side view of the inter-vertebral cage 300 in the second shape 328, wherein the legs 306-309 are substantially parallel to each other, and the closeout 305 is angled slightly downward. Upon insertion of the legs 306 and 308 into the first location on the first vertebra 380, and the insertion of the legs 307 and 309 into the second location on the second vertebra 381, the body 304 moves between the vertebrae 380 and 381, until the second engagement surfaces 346 and 349 contact the respective vertebra 380 or 381. Upon full insertion, the spacing member 301 and the engagement plates 302 and 303 are disposed between the vertebrae 380 and 381. In this position, the closeout 305 does not contact the second engagement plate 303. Upon the application of energy to the legs 306-309, the legs 306-309 move from the second shape 328 to the first shape 327, thereby drawing the legs 306-309 toward the inter-vertebral cage 300, and further securing the inter-vertebral cage 300 to the vertebrae 380 and 381. Upon the application of energy to the body 304, the bends 337 and 338 extend to the first shape 327, thereby drawing the second engagement plate 303 away from the first engagement plate 302.

The closeout 305 similarly moves from the second shape 328 to the first shape 327, thereby extending towards the second engagement plate 303 until the closeout 305 contacts the extended engagement plate 303. At this point, the cavity 314 is substantially closed out, as shown in FIG. 17B. While this embodiment has been shown with bone graft material being inserted after the application of energy to the body 304 of the inter-vertebral cage 300, one of ordinary skill in the art will recognize that bone graft material may be inserted into the cavity 314 at alternate times, or not at all.

In an extension of the third embodiment, an inter-vertebral cage 390 is similar in form and function to the inter-vertebral cage 300; however, the inter-vertebral cage 390 does not include an integral closeout, as shown in FIGS. 19A-19C. Accordingly, like parts have been labeled with like numerals. As shown in FIG. 19A, the inter-vertebral cage 390 additionally includes an inner surface 392 disposed on a side of the first engagement plate 302 closest to the cavity 314, an inner surface 393 disposed on a side of the second engagement plates 302 closest to the cavity 314, a first retention feature 391 and a second retention feature 394 disposed on the inner surfaces 392-393. In this specific example, the retention features 391 and 394 are raised features that are disposed on each surface. The second retention feature 394 is disposed at a predetermined distance from the first retention feature 391. The retention features 391 and 394 are disposed in alignment with the opposing pair, and are located in proximity to the location of the integral closeout of the previous embodiments. In this fashion, an object may be retained between the retention features 391 and 394. While this embodiment has been shown with two retention features 391 and 394, one of ordinary skill in the art will recognize that a multitude of retention features or retention feature designs, included but not limited to tabs, slots, threads, and grooves, at a predetermined spacing may be utilized.

As shown in FIG. 19B, the closeout 395 is a separate component and is similarly constructed from shape memory material. Though one skilled in the art would recognize that non-shape memory materials could be used for the closeout to maintain the separation of the engagement plates 302 and 303. Accordingly, the closeout 395 includes a first shape 396 and a second shape 397. In this specific example, in the first shape 396 the closeout 395 is planar in shape, and is of a length 398 that is complementary to a distance between the retention features 391 and 394 disposed on the first engagement plate 302 and the second engagement plate 303. In the second shape 397, the closeout 395 deformed to a curved shape, and a length 399. In this example, the length 399 is shorter than the length 398, and therefore may fit between the highest parts of the retention features 391 and 394.

Figure 20:
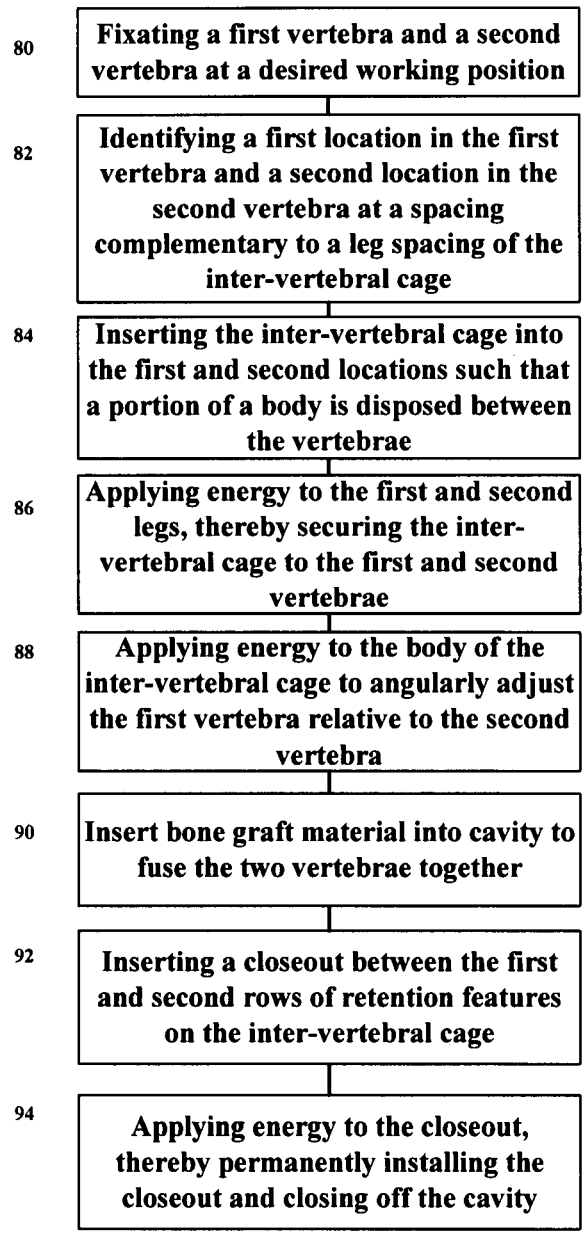
FIG. 20 provides a flowchart illustrating the method steps for utilizing the inter-vertebral cage according to the extension of the third embodiment.

Use of the inter-vertebral cage 390 is substantially identical to the inter-vertebral cage 300, however, two additional steps are required. As shown in the method flowchart of FIG. 20, the process commences with step 80, wherein a first vertebra 380 and a second vertebra 381 are fixated at a desired working position. In step 82, a first securing location is identified in the first vertebra 380, and a second securing location is identified in the second vertebra 381. The inter-vertebral cage 390 is inserted into the first and second securing locations of the first and second vertebrae 380 and 381 utilizing any of the methods previously disclosed, step 84. Once inserted, energy is applied to the legs 306-309 to secure the inter-vertebral cage 390 to the first and second vertebrae 380 and 381, step 86. Energy is then applied to the body 304 of the inter-vertebral cage 390 to reorient the first and second vertebrae 380 and 381, step 88. Next, step 90, bone graft is inserted into the cavity 314. The process then requires the insertion of the closeout 395 in the second shape 397 between the first and second retention features 391 and 394, step 92. Energy is then applied to the closeout 395 to force the closeout 395 to move from the second shape 397 to the first shape 396, thereby extending the length 399 of the closeout 395 to length 398, step 94. Upon the application of energy to the closeout 395, the closeout 395 must be guided between the first and second retention features 391 and 394. Once extended, the closeout is permanently installed between the retention features 391 and 394, and the first and second engagement plates 302 and 303, thereby closing out the cavity 314, providing load bearing capability between the engagement plates 302 and 303, and aiding in the retention of bone graft material in the cavity 314. While the method of implanting inter-vertebral cage 390 has been presented, one of ordinary skill in the art will recognize that the sequence of steps may be changed to meet a specific clinical need.

While the non-integral closeout 395 has been shown as an extension of the third embodiment, one of ordinary skill in the art will recognize that the use of a non-integral closeout 395 is possible with all embodiments of this invention.

Figure 21A:
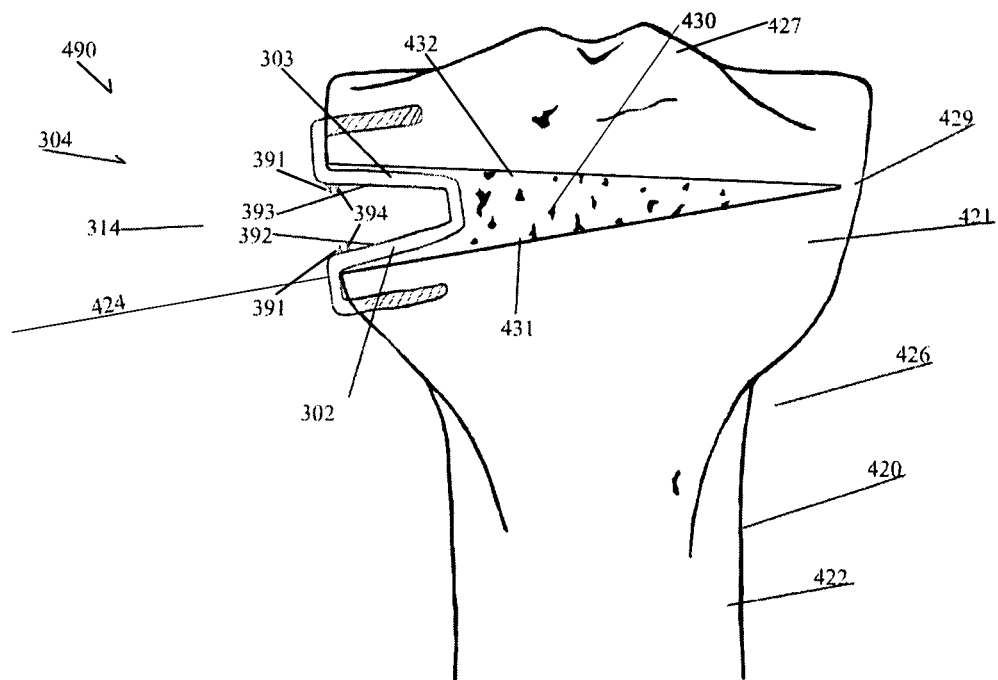
FIG. 21A provides a section view of a cage in a second shape utilized in a tibia end portion adjustment operation according to a fourth embodiment.

In a fourth embodiment a cage 490 is utilized in an opening wedge osteotomy to change the angulation of an end portion of a tibia 420. The cage 490 is similar in form and function to the inter-vertebral cage 390 according to the extension of the third embodiment that does not include an integral closeout. Accordingly, like parts have been referenced with like numerals. As shown in FIG. 21A, the cage 490 includes the inner surface 392 disposed on a side of the first engagement plate 302 closest to the cavity 314, the inner surface 393 disposed on a side of the second engagement plate 303 closest to the cavity 314, the first retention feature 391 and the second retention feature 394 disposed on the inner surfaces 392-393. In this specific example, the retention features 391 and 394 are raised features that are disposed on each surface. The second retention feature 394 is disposed at a predetermined distance from the first retention feature 391. The retention features 391 and 394 are disposed in alignment with the opposing pair, and are located in proximity to the location of the integral closeout of the previous embodiments. In this fashion, an object may be retained between the retention features 391 and 394. While this embodiment has been shown with two retention features 391 and 394, one of ordinary skill in the art will recognize that a multitude of retention features or retention feature designs, included but not limited to tabs, slots, threads, and grooves, at a predetermined spacing may be utilized. Further, one of ordinary skill in the art will recognize that if the strength of the shape memory metal or the bone graft placed between the vertebrae, for all embodiments of the spinal cage, or for this fourth embodiment, for use in an osteotomy is high, a closeout or retention features will not be needed to resist the functional loading of the bone. The need for a closeout would also be eliminated if the length of the engagement plates 302 and 303 were short, or other implants outside the scope of this invention were intended for use in the procedure so as to share the functional load of the bone.

Figure 21B:
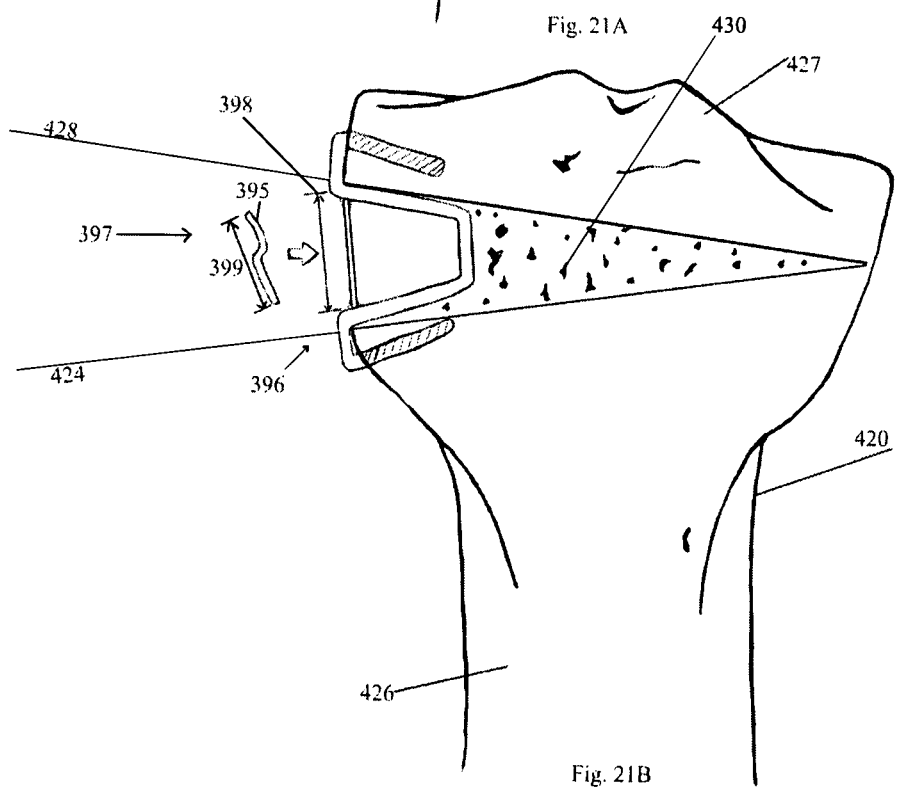
FIG. 21B provides a section view of a cage in a first shape utilized in a tibia end portion adjustment operation according to the fourth embodiment.

As shown in FIG. 21B, the closeout 395 is a separate component and is similarly constructed from shape memory material. Accordingly, the closeout 395 includes a first shape 396 and a second shape 397. In this specific example, in the first shape 396, the closeout 395 is planar in shape, and is of a length 398 that is complementary to a distance between the retention features 391 and 394 disposed on the first engagement plate 302 and the second engagement plate 303. In the second shape 397, the closeout 395 is deformed to a curved shape, and a length 399. In this example, the length 399 is shorter than the length 398, and therefore may fit between the highest parts of the retention features 391 and 394.

As shown if FIG. 21A, the tibia 420 includes a tubular portion 422 connected to a knuckle portion 421. The knuckle portion 421 is severed at an adjustment plane 424, up to the point where only a small segment remains connected on the opposite end of the knuckle portion 421, thereby creating a first bone 426 and a second bone 427. The first bone 426 includes a bone working face 431 and the second bone 427 includes an end portion adjusting face 432 disposed on the partially connected second bone 427. The partially connected second bone 427 hinges about a connection point 429, and is rotated away from the adjustment plane 424, such that the cage 490 may be impacted or inserted into a position between the first bone 426 and the second bone 427. Installation and operation of the cage 490 is substantially identical to the installation and operation of the cage 390, however, additional steps may be required in the current application. Illustratively, in this embodiment, the legs 306-307 of the cage 490 are impacted into the partially connected second bone 427 and the knuckle portion 421 of the first bone 426, such that the body 304 is disposed between the end portion adjusting face 432 and the bone working face 431. Upon the application of activation energy, the legs 306-307 of the cage 490 move toward their respective engagement plates 302 or 303 to secure the cage 490 to the first and second bones 426-427. Upon the application of activation energy to the body 304, the engagement plates 302-303 move toward each other to align the end portion adjusting face 432 with a desired corrective plane 428. After the desired position has been reached, the closeout 395 is inserted between the retention features 391 and 394, and energized, such that the closeout 395 supports the cage 490 in the vertical direction.

Figure 22:
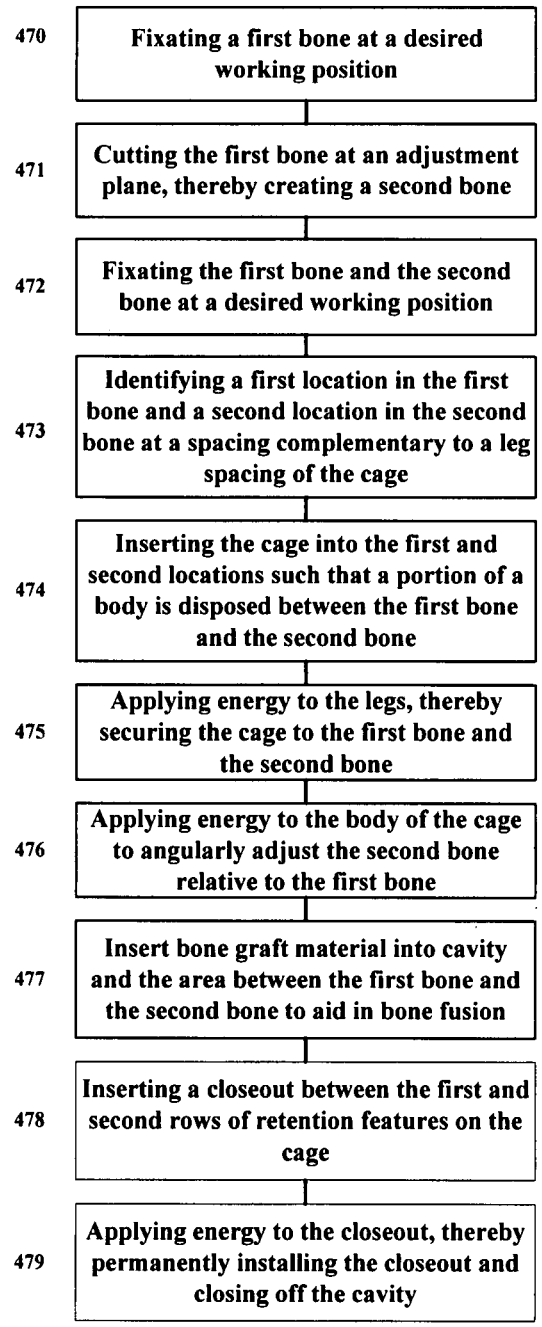
FIG. 22 provides a flowchart illustrating the method steps for utilizing the cage according to the fourth embodiment.
Figure 23A:
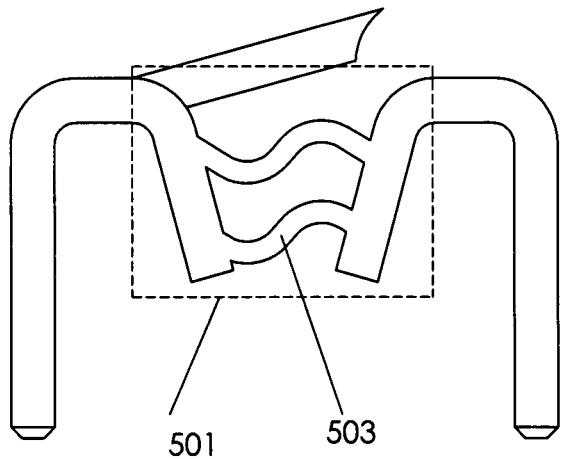
FIG. 23A provides a front view of a cage having a spacing member and a closeout disposed on an inner faces of the engagement plates according to a fifth embodiment.
Figure 23B:
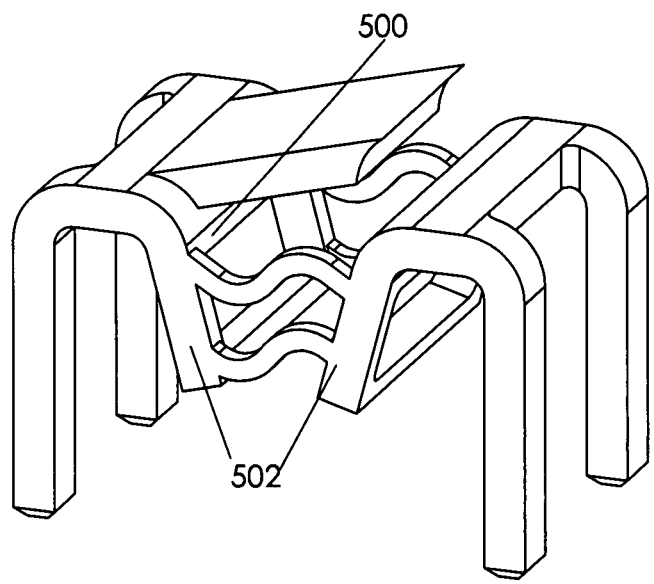
FIG. 23B provides a perspective view of the cage having a spacing member and a closeout disposed on an inner faces of the engagement plates according to the fifth embodiment.
Figure 23C:
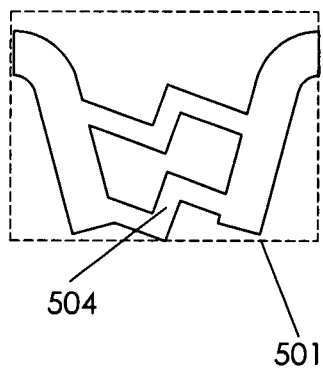
FIG. 23C provides a front view of a spacing member having "Z" shaped expansion members according to the fifth embodiment.
Figure 23D:
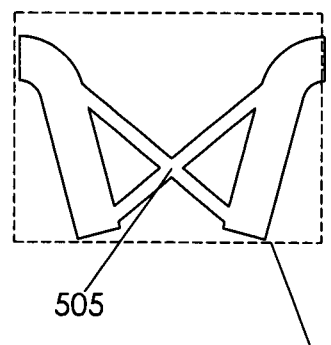
FIG. 23D provides a front view of a spacing member having interlaced expansion members according to the fifth embodiment.
Figure 23E:
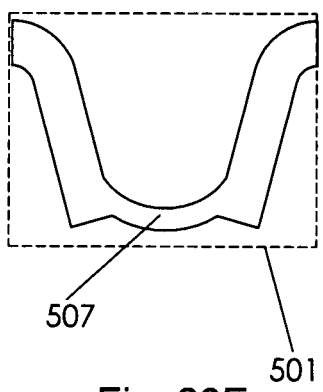
FIG. 23E provides a front view of a spacing member having "C" shaped expansion members according to the fifth embodiment.
Figure 23F:
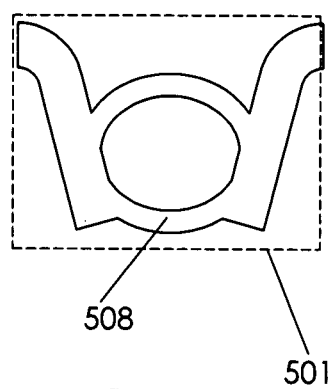
FIG. 23F provides a front view of a spacing member having "O" shaped expansion members according to the fifth embodiment.
Figure 23G:
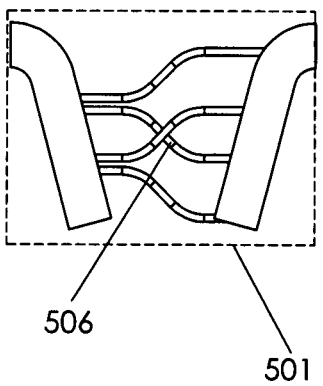
FIG. 23G provides a front view of a spacing member having interlaced expansion members according to the fifth embodiment.

Use of the cage 490 is substantially identical to the inter-vertebral cage 390, however additional steps are required in the tibial end portion adjustment operation. As shown in the method flowchart of FIG. 22, the process commences with step 470, wherein a surgeon fixates the first bone 426 at a desired working position. The process continues with the severing of the first bone 426 at an adjustment plane 424, such that only a small portion remains connected to the first bone 426, thereby forming a partially connected second bone 427, step 471. In step 472, the surgeon fixates the partially connected second bone 427 and the first bone 426 at a desired working position. In step 473, the surgeon identifies a first location in the first bone 426 and a second location in the partially connected second bone 427, at a spacing complementary to a leg spacing of the cage 490. The cage 490 is inserted into the first and second securing locations of the first bone 426 and the second bone 427 utilizing any of the methods previously disclosed, step 474. Once inserted, energy is applied to the legs 306-309 to secure the cage 490 to the first bone 426 and the partially connected second bone 427, step 475. Energy is then applied to the body 304 of the cage 490 to reorient the partially connected second bone 427 relative to the first bone 426, step 476. Next, in step 477, bone graft material 430 is inserted into the cavity 314 of the cage 490 and between the bone working face 431 and the end portion adjusting face 432 to promote bone fusion.

The process then requires the insertion of the closeout 395 in the second shape 397 between the first and second retention features 391 and 394, step 478. Energy is then applied to the closeout 395 to force the closeout 395 to move from the second shape 397 to the first shape 396, thereby extending the length 399 of the closeout 395 to the length 398, step 479. Upon the application of energy to the closeout 395, the closeout 395 must be guided between the first and second retention features 391 and 394. Once extended, the closeout 395 is permanently installed between the retention features 391 and 394, and the first and second engagement plates 302 and 303, thereby closing out the cavity 314, providing load bearing capability between the engagement plates 302 and 303, and aiding in the retention of bone graft material in the cavity 314.

While this embodiment has been shown with a partial cut through the knuckle portion 421 of a tibia 420, one of ordinary skill in the art will recognize that the methods described in this fourth embodiment may be applicable to fully severed bones, partially severed bones, or the like. One of ordinary skill in the art will further recognize that cage 490 and its methods may be applicable to bones other than tibia bones, and that the sizes, lengths, displacements, and angles of the cage or cage components may be adjusted for use in specific applications, as described in the embodiments of this disclosure.

One of ordinary skill in the art will further recognize the preferred embodiment and each alternate embodiment could accomplish the same function and have the same design features through apertures 110 and 111 that are holes, slots, grooves, an irregular opening or an open mesh structure.

Additionally, one of ordinary skill in the art will further recognize that the spacing member 101 planar section 109 of the preferred embodiment and all similar design features of each alternate embodiment could be located not on the first ends 118 and 121 but between the engagement plates 102 and 103 at a number of different locations along its inner face 500 or periphery 502, as shown in FIG. 23 A-G. At this location the spacing member 501, allows a number of designs for the shape changing members that distract, contract or change the angle of the first and second bones. Finally, this skill in the art would understand that the expansion or contraction nature of the planar section 109 in each of the embodiments could be achieved not by having a curved section that straightened but by having a planar section that was cut into several members spanning the engagement plates 102 to 103 where these members were "S" 503, "Z" 504 or interlaced 505 or 506 so that in the first shape they were straight and in the second shape they returned to their contracted "S", "Z" or interlaced shape so as to contract spacing member 501 or alternatively they are straight in the first shape and "S", "Z" or interlaced in their second shape so as to straighten to cause expansion of the cage and separation of bone. The expansion and contraction members can be selected from the family of shapes that include but are not limited to "S", "Z", "C", "O" 508 or "C" 507 shaped.

Although the present invention has been described in terms of the foregoing preferred embodiment, such description has been for exemplary purposes only and, as will be apparent to those of ordinary skill in the art in light of the multiple alternate embodiments that many alternatives, equivalents, and variations of varying degrees will fall within the scope of the present invention. That scope, accordingly, is not to be limited in any respect by the foregoing detailed description; rather, it is defined only by the claims that follow.

We claim:
1. A cage comprising:
a body adapted for insertion into a space between a first bone and a second bone,
wherein the body comprises shape memory material and is adapted to transition to an end use shape upon the application of energy thereto, and
wherein the body comprises
a first engagement plate,
a second engagement plate, and
a spacing member coupling the first engagement plate with the second engagement plate;
a first leg secured to the body and adapted to engage a portion of the first bone exterior to the space;
a second leg secured to the body and adapted to engage a portion of the second bone exterior to the space; and
a closeout comprised of shape memory material disposed on the first engagement plate, wherein, upon the application of energy to the body, the closeout extends and contacts the second engagement plate, thereby closing out and retaining bone graft material in a cavity disposed between the first and second engagement plates.
2. The cage according to claim 1, wherein the closeout is load bearing.

* * * * *